United States Patent
Chong et al.

(10) Patent No.: US 9,393,363 B2
(45) Date of Patent: Jul. 19, 2016

(54) INSERTION DEVICE SYSTEMS AND METHODS

(75) Inventors: Colin A. Chong, Burbank, CA (US); Eric M. Lorenzen, Granada Hills, CA (US); Rafael Bikovsky, Oak Park, CA (US); Arsen Ibranyan, Glendale, CA (US); Julian D. Kavazov, Arcadia, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 0 days.

(21) Appl. No.: 12/649,172

(22) Filed: Dec. 29, 2009

(65) Prior Publication Data

US 2011/0054400 A1    Mar. 3, 2011

Related U.S. Application Data

(62) Division of application No. 12/553,038, filed on Sep. 2, 2009.

(51) Int. Cl.
| | | |
|---|---|---|
| A61M 37/00 | (2006.01) | |
| A61M 5/142 | (2006.01) | |
| A61M 5/158 | (2006.01) | |
| A61M 5/14 | (2006.01) | |
| A61M 5/145 | (2006.01) | |

(52) U.S. Cl.
CPC ........... *A61M 5/14248* (2013.01); *A61M 5/158* (2013.01); *A61M 5/1413* (2013.01); *A61M 5/1456* (2013.01); *A61M 2005/14252* (2013.01); *A61M 2005/14268* (2013.01); *A61M 2005/1583* (2013.01); *A61M 2005/1585* (2013.01); *A61M 2209/045* (2013.01); *Y10T 29/49826* (2015.01)

(58) Field of Classification Search
CPC ......... A61M 2005/14252; A61M 2005/14268; A61M 2005/1583; A61M 2005/1585; A61M 2209/045; A61M 5/1413; A61M 5/14248; A61M 5/1456; A61M 5/158; Y10T 29/49826
USPC .......................................... 604/131
See application file for complete search history.

(56) References Cited

U.S. PATENT DOCUMENTS

| | | | |
|---|---|---|---|
| 3,701,345 A | | 10/1972 | Heilman et al. |
| 3,884,230 A | * | 5/1975 | Wulff ............................ 604/198 |
| 3,994,295 A | * | 11/1976 | Wulff ............................ 604/241 |
| 4,633,232 A | | 12/1986 | Nelson et al. |
| 5,122,123 A | | 6/1992 | Vaillancourt |

(Continued)

FOREIGN PATENT DOCUMENTS

| | | |
|---|---|---|
| DE | 31 44 825 | 5/1983 |
| EP | 0 0 927 12 | 11/1983 |

(Continued)

OTHER PUBLICATIONS

Partial Search Report dated Mar. 1, 2011 from related patent application No. PCT/US2010/060892.

(Continued)

*Primary Examiner* — Jason Flick
(74) *Attorney, Agent, or Firm* — Foley & Lardner LLP

(57) ABSTRACT

A piercing member for piercing a membrane may be arranged within a housing and supported by a compliant that may be for allowing articulation of the piercing member relative to the housing in a case where the piercing member is in the membrane and moved relative to the housing.

29 Claims, 22 Drawing Sheets

(56) References Cited

U.S. PATENT DOCUMENTS

| | | | |
|---|---|---|---|
| 5,176,662 A | 1/1993 | Bartholomew et al. |
| 5,236,416 A | 8/1993 | McDaniel et al. |
| 5,334,188 A | 8/1994 | Inoue et al. |
| 5,533,981 A | 7/1996 | Mandro et al. |
| 5,628,309 A | 5/1997 | Brown |
| 5,662,612 A | 9/1997 | Niehoff |
| 5,954,697 A | 9/1999 | Srisathapat et al. |
| 6,283,943 B1 | 9/2001 | Dy et al. |
| 6,299,131 B1 | 10/2001 | Ryan |
| 6,416,402 B1 | 7/2002 | Moore |
| 6,423,035 B1 | 7/2002 | Das et al. |
| 6,461,329 B1 | 10/2002 | Van Antwerp et al. |
| 6,699,218 B2 | 3/2004 | Flaherty et al. |
| 6,727,689 B1 | 4/2004 | Furlong et al. |
| 6,740,059 B2 | 5/2004 | Flaherty |
| 6,749,587 B2 | 6/2004 | Flaherty |
| 6,830,558 B2 | 12/2004 | Flaherty et al. |
| 6,945,760 B2 | 9/2005 | Gray et al. |
| 6,960,192 B1 | 11/2005 | Flaherty et al. |
| 7,018,360 B2 | 3/2006 | Flaherty et al. |
| 7,396,353 B2 * | 7/2008 | Lorenzen et al. ......... 604/891.1 |
| 7,811,279 B2 | 10/2010 | John |
| 7,935,104 B2 | 5/2011 | Yodfat et al. |
| 8,105,279 B2 | 1/2012 | Mernoe et al. |
| 8,152,771 B2 | 4/2012 | Mogensen et al. |
| 8,308,679 B2 | 11/2012 | Hanson et al. |
| 8,435,209 B2 | 5/2013 | Hanson et al. |
| 8,858,500 B2 | 10/2014 | Hanson et al. |
| 8,882,710 B2 | 11/2014 | Chong et al. |
| 8,900,190 B2 | 12/2014 | Chong et al. |
| 8,998,840 B2 | 4/2015 | Hanson et al. |
| 8,998,858 B2 | 4/2015 | Chong et al. |
| 9,039,653 B2 | 5/2015 | Chong et al. |
| 9,039,659 B2 | 5/2015 | Hanson et al. |
| 2001/0034506 A1 | 10/2001 | Hirschman et al. |
| 2001/0041869 A1 | 11/2001 | Causey et al. |
| 2004/0002682 A1 | 1/2004 | Kovelman et al. |
| 2004/0162521 A1 | 8/2004 | Bengtsson |
| 2005/0065472 A1 | 3/2005 | Cindrich et al. |
| 2005/0101932 A1 | 5/2005 | Cote et al. |
| 2006/0061353 A1 | 3/2006 | Etherington et al. |
| 2006/0079765 A1 | 4/2006 | Neer et al. |
| 2006/0200020 A1 | 9/2006 | Brister et al. |
| 2007/0049865 A1 | 3/2007 | Radmer et al. |
| 2007/0060871 A1 | 3/2007 | Istoc et al. |
| 2007/0073236 A1 | 3/2007 | Mernoe et al. |
| 2007/0156094 A1 | 7/2007 | Safabash et al. |
| 2007/0191702 A1 | 8/2007 | Yodfat et al. |
| 2007/0191770 A1 | 8/2007 | Moberg et al. |
| 2007/0270744 A1 | 11/2007 | Dacquay et al. |
| 2008/0024812 A1 | 1/2008 | Miyazaki et al. |
| 2008/0051697 A1 | 2/2008 | Mounce et al. |
| 2008/0051711 A1 | 2/2008 | Mounce et al. |
| 2008/0051714 A1 * | 2/2008 | Moberg et al. ............... 604/135 |
| 2008/0077081 A1 | 3/2008 | Mounce et al. |
| 2008/0097321 A1 * | 4/2008 | Mounce et al. ............... 604/132 |
| 2008/0097328 A1 | 4/2008 | Moberg et al. |
| 2008/0097381 A1 | 4/2008 | Moberg et al. |
| 2008/0269687 A1 | 10/2008 | Chong et al. |
| 2008/0281270 A1 | 11/2008 | Cross et al. |
| 2008/0319394 A1 | 12/2008 | Yodfat et al. |
| 2008/0319414 A1 | 12/2008 | Yodfat et al. |
| 2009/0054810 A1 | 2/2009 | Zanzucchi et al. |
| 2009/0069750 A1 * | 3/2009 | Schraga ................ 604/167.02 |
| 2009/0156990 A1 | 6/2009 | Wenger et al. |
| 2009/0182301 A1 * | 7/2009 | Bassarab et al. ............. 604/416 |
| 2009/0259183 A1 | 10/2009 | Chong et al. |
| 2009/0259198 A1 | 10/2009 | Chong et al. |
| 2009/0264825 A1 * | 10/2009 | Cote et al. .................... 604/158 |
| 2009/0326458 A1 | 12/2009 | Chong et al. |
| 2010/0070878 A1 | 3/2010 | Amento et al. |
| 2010/0137790 A1 | 6/2010 | Yodfat |
| 2010/0152658 A1 | 6/2010 | Hanson et al. |
| 2010/0274180 A1 | 10/2010 | Donovan et al. |
| 2011/0025715 A1 | 2/2011 | Uchida et al. |
| 2011/0166512 A1 | 7/2011 | Both et al. |
| 2011/0178461 A1 | 7/2011 | Chong et al. |
| 2011/0213306 A1 | 9/2011 | Hanson et al. |
| 2012/0130312 A1 | 5/2012 | Mernoe et al. |
| 2012/0215163 A1 | 8/2012 | Hanson et al. |
| 2013/0253422 A1 | 9/2013 | Hanson et al. |

FOREIGN PATENT DOCUMENTS

| | | |
|---|---|---|
| EP | 0 317 808 A2 | 5/1989 |
| EP | 0 937 475 | 8/1999 |
| EP | 1177802 | 2/2002 |
| EP | 1 752 172 | 8/2005 |
| EP | 2 077 128 B1 | 12/2010 |
| EP | 2 375 342 A2 | 10/2011 |
| GB | 2 327 151 | 1/1999 |
| JP | 11-339439 | 12/1999 |
| KR | 100692005 B1 | 3/2007 |
| KR | 1020090106755 A | 10/2009 |
| WO | WO-86/02562 | 5/1986 |
| WO | WO-99/33504 | 7/1999 |
| WO | WO-00/47254 | 8/2000 |
| WO | WO-01/68163 | 9/2001 |
| WO | WO-2006/031500 | 3/2006 |
| WO | WO-2006/076656 | 7/2006 |
| WO | WO-2006/121921 A2 | 11/2006 |
| WO | WO-2006/122406 | 11/2006 |
| WO | WO-2006/124756 | 11/2006 |
| WO | WO-2008/024810 | 2/2008 |
| WO | WO-2008/024812 A2 | 2/2008 |
| WO | WO-2008/024814 A2 | 2/2008 |
| WO | WO-2008/078318 | 7/2008 |
| WO | WO-2008/092782 | 8/2008 |
| WO | WO-2008/133702 A1 | 11/2008 |
| WO | WO-2009/001346 | 12/2008 |
| WO | WO-2009/016638 | 2/2009 |
| WO | WO-2009/033032 A1 | 3/2009 |
| WO | WO-2009/066288 | 5/2009 |
| WO | WO-2009/093759 A1 | 7/2009 |
| WO | WO-2009/098291 A1 | 8/2009 |
| WO | WO-2009/106517 | 9/2009 |
| WO | WO-2009/125398 A2 | 10/2009 |
| WO | WO-2009/135667 | 11/2009 |
| WO | WO-2009/144726 A1 | 12/2009 |
| WO | WO-2011-082256 | 7/2011 |
| WO | WO-2011/090629 | 7/2011 |
| WO | WO-2011/119768 | 9/2011 |

OTHER PUBLICATIONS

Partial Search Report dated Mar. 21, 2011 from related patent application No. PCT/US2010/060895.
Partial Search Report dated Mar. 23, 2011 from related patent application No. PCT/US2010/047590.
International Search Report and Written Opinion from related patent application No. PCT/US2010/062414.
IPRP dated Mar. 6, 2012 from related PCT/US2010/047590 application.
Search Report dated Jul. 13, 2011 from related PCT application No. PCT/US2010/060895.
Partial International Search Report from related PCT application No. PCT/US2012/064454, mailed Feb. 4, 2013, 5 pages.
International Search Report for PCT/US2011/066504, dated Jul. 6, 2012.
English Abstract of DE3144825, 2 pages.
English Abstract of EP0092712, 1 page.
English Abstract of EP1752172, 1 page.
International Search Report and Written Opinion from related PCT application No. PCT/US2011/066501, mailed Dec. 12, 2012, 23 pages.
International Search Report and Written Opinion from related PCT application No. PCT/US2011/066504, mailed Oct. 24, 2012, 29 pages.
International Search Report and Written Opinion from related PCT application No. PCT/US2012/022881, mailed Aug. 28, 2012, 21 pages.

(56) References Cited

OTHER PUBLICATIONS

International Search Report and Written Opinion from related PCT application No. PCT/US2012/022883, mailed Aug. 7, 2012, 21 pages.
International Search Report and Written Opinion from related PCT application No. PCT/US2012/055661, mailed Dec. 11, 2012, 11 pages.
U.S. Notice of Allowance from related U.S. Appl. No. 13/235,228, mailed Dec. 20, 2012, 12 pages.
U.S. Non-Final Office Action from related U.S. Appl. No. 12/553,038, mailed Dec. 28, 2012, 10 pages.
U.S. Office Action from related U.S. Appl. No. 12/553,038, mailed Jun. 20, 2013.
U.S. Office Action from related U.S. Appl. No. 13/103,014, mailed May 22, 2013.
International Search Report and Written Opinion from related PCT application No. PCT/US2012/064454, mailed Jun. 12, 2013.
US Notice of Allowance dated Jul. 7, 2014, from related U.S. Appl. No. 12/650,287.
US Notice of Allowance dated Jul. 24, 2014, from related U.S. Appl. No. 13/015,028.
US Office Action dated Jul. 1, 2014, from related U.S. Appl. No. 12/974,106.
U.S. Notice of Allowance dated Oct. 20, 2014, from related U.S. Appl. No. 12/974,106.
U.S. Office Action dated Oct. 9, 2014, from related U.S. Appl. No. 12/974,117.
U.S. Office Action dated Sep. 5, 2014, from related U.S. Appl. No. 12/650,378.
U.S. Notice of Allowance dated Sep. 22, 2014, from related U.S. Appl. No. 13/015,051.
U.S. Office Action dated Sep. 11, 2014, from related U.S. Appl. No. 13/462,752.
U.S. Office Action dated Sep. 8, 2014, from related U.S. Appl. No. 13/421,564.
U.S. Notice of Allowance dated Feb. 2, 2015, from related U.S. Appl. No. 12/974,117.
International Search Report and Written Opinion dated Sep. 6, 2011, from related international application No. PCT/US2010/047590.
Japanese Office Action from related Japanese Patent Application No. 2012-528022, issued Jun. 25, 2013.
Partial International Search Report dated Apr. 16, 2012, from related international application No. PCT/US2011/066504.
Partial International Search Report dated Jun. 7, 2011, from related international application No. PCT/US2010/062414.
Partial Search Report dated Jul. 9, 2012, from related international patent application No. PCT/US2011/066501.
U.S. Office Action dated Jan. 16, 2015, from related U.S. Appl. No. 13/462,752.
US Notice of Allowance Aug. 1, 2014, from related U.S. Appl. No. 12/553,038.
US Notice of Allowance dated Jan. 21, 2015, from related U.S. Appl. No. 13/412,564.
US Notice of Allowance dated Jan. 21, 2015, from related U.S. Appl. No. 13/421,564.
US Notice of Allowance dated Sep. 19, 2012, from related U.S. Appl. No. 12/649,619.
US Notice of Allowance dated Sep. 25, 2015, from related U.S. Appl. No. 13/103,014.
US Notice of Allowance on U.S. Appl. No. 12/650,378 dated Dec. 19, 2014.
US Office Action dated Aug. 1, 2012, from related U.S. Appl. No. 13/015,028.
US Office Action dated Aug. 16, 2012, from related U.S. Appl. No. 12/649,619.
US Office Action dated Aug. 2, 2012, from related U.S. Appl. No. 12/974,106.
US Office Action dated Aug. 2, 2012, from related U.S. Appl. No. 13/015,051.
US Office Action dated Dec. 19, 2013, from related U.S. Appl. No. 13/421,564.
US Office Action dated Dec. 22, 2011, from related U.S. Appl. No. 12/649,619.
US Office Action dated Feb. 2, 2012, from related U.S. Appl. No. 12/553,038.
US Office Action dated Jan. 16, 2015, from related U.S. Appl. No. 13/791,773.
US Office Action dated Jan. 29, 2016, from related U.S. Appl. No. 13/791,773.
US Office Action dated Jul. 16, 2015, from related U.S. Appl. No. 13/103,014.
US Office Action dated Jul. 20, 2012, from related U.S. Appl. No. 12/553,038.
US Office Action dated Jul. 20, 2012, from related U.S. Appl. No. 12/650,378.
US Office Action dated Jun. 18, 2012, from related U.S. Appl. No. 12/650,287.
US Office Action dated May 28, 2015, from related U.S. Appl. No. 13/462,752.
US Office Action dated Nov. 6, 2013, from related U.S. Appl. No. 13/462,752.
US Office Action dated Sep. 11, 2014, from related U.S. Appl. No. 13/462,752.
US Office Action dated Sep. 30, 2015, from related U.S. Appl. No. 13/462,752.
US Office Action dated Sep. 8, 2014, from related U.S. Appl. No. 13/421,564.
Partial Search Report dated May 4, 2012, from related international application No. PCT/US2012/022881.
US Office Action dated Aug. 2, 2012, from related U.S. Appl. No. 12/974,117.
US Office Action dated Feb. 10, 2016, from related U.S. Appl. No. 13/462,752.
US Notice of Allowance dated May 20, 2016, from related U.S. Appl. No. 13/103,014.
US Office Action dated Apr. 25, 2016, from related U.S. Appl. No. 13/900,463.
US Office Action dated Jun. 1, 2016, from related U.S. Appl. No. 13/791,773.

* cited by examiner

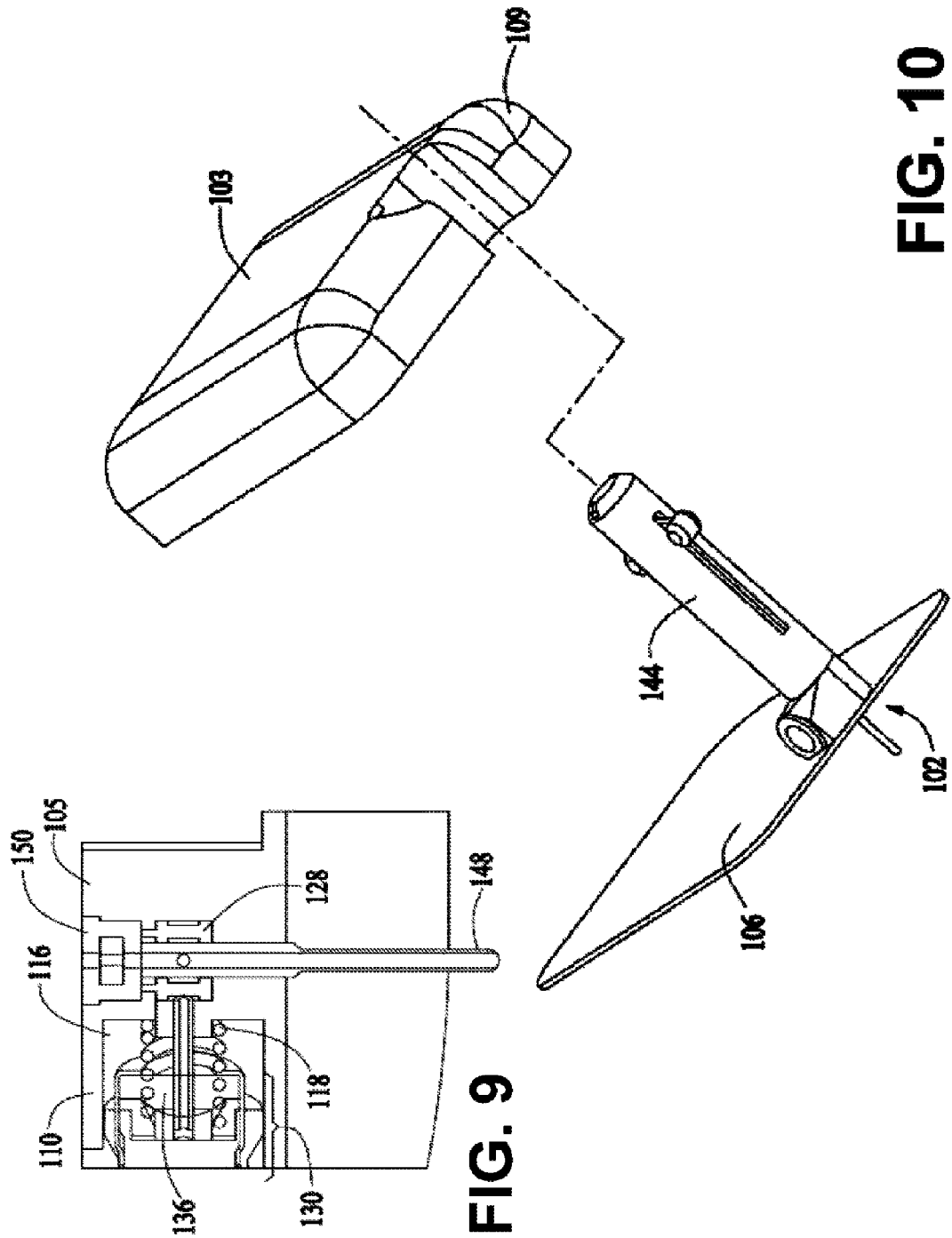

INSERTION DEVICE SYSTEMS AND METHODS

CROSS-REFERENCE TO RELATED PATENT APPLICATION

This application is a Divisional of U.S. application Ser. No. 12/553,038, filed Sep. 2, 2009, incorporated herein by reference in its entirety.

BACKGROUND

1. Field of the Invention

Embodiments of the present invention relate generally to insertion device systems and methods and, in specific embodiments, to insertion device systems and methods for insertion into a patient.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. Further examples of various insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

An insertion system in accordance with an embodiment of the present invention may include, but is not limited to, a base, a first device housing, and a second device housing. The base may be adapted to be carried by a patient. The first device housing may be configured to be operatively engaged with and disengaged from the base.

The first device housing may include a first carrier body. The first carrier body may be arranged for movement within at least a portion of the first device housing at least between a retracted position and an advanced position. The first carrier body may be for supporting a piercing member in a position orientated for insertion through skin of the patient upon movement of the first carrier body from the retracted position to the advanced position.

The second device housing may be configured to be operatively engaged with and disengaged from the first device housing. The second device housing may include a second carrier body and a driver. The second carrier body may be arranged for movement within at least a portion of the second device housing at least between a retracted position and an advanced position. The second carrier body may be operatively connectable with the first carrier body. The driver may be arranged within the second device housing to move the first carrier body from the retracted position toward the advanced position to insert at least a portion of the piercing member through skin of the patient.

In various embodiments, the driver may be arranged within the second device housing to move the second carrier body from the retracted position toward the advanced position to move the first carrier body from the retracted position toward the advanced position to insert at least a portion of the piercing member through skin of the patient. In various embodiments, the insertion system may further include a locking mechanism. The locking mechanism may be adapted to operatively engage at least one of the driver and the second carrier body and to substantially prevent premature release of the carrier body before securing the insertion system in position against the skin of the patient.

In various embodiments, the first carrier body may be configured to operatively engage the base when the first carrier body is moved to the advanced position. In some embodiments, the first carrier body may be configured to disengage the first device housing from the base upon the first carrier body being moved to the advanced position.

In further embodiments, one of the base and the first device housing may have an aperture. The other of the base and the first device housing may have a lever for engaging the aperture to operatively engage the first device housing to the base. The first carrier body may have at least one protrusion for disengaging the lever from the aperture upon the first carrier body being moved to the advanced position.

In various embodiments, one of the base and the first device housing may have an aperture. The other of the base and the first device housing may have a lever for engaging the aperture to operatively engage the first device housing to the base. In various embodiments, the first carrier body may include a plunger. The plunger may be configured to support the piercing member, and to insert the piercing member in the skin of the user-patient upon movement of the first carrier body from the retracted position to the advanced position.

In various embodiments, a distance traveled by the first carrier body relative to the first device housing from the retracted position to the advanced position may be equal to at least a distance traveled by the second carrier body relative to the second device housing from the retracted position to the advanced position. In various embodiments, a distance traveled by the first carrier body relative to the first device housing from the retracted position to the advanced position may be equal to at least a distance required to insert the piercing member into the skin of the patient.

In various embodiments, the first carrier body may include a plunger and a collar body. The collar body may be operatively connected to the plunger. The piercing member may be supported by at least one of the plunger and the collar body in a position orientated for insertion through the skin of the patient upon movement of the first carrier body from the retracted position to the advanced position.

In some embodiments, the piercing member may comprise a cannula supported by the collar body and a needle supported by the plunger. The needle may be disposed at least partially through the cannula. The cannula and the needle may be supported in a position orientated for insertion through the skin of the patient upon movement of the first carrier body from the retracted position to the advanced position.

In further embodiments, the plunger and the needle may be removable from the collar body. The cannula and the collar body may be adapted for reuse with another collar body and cannula. In further embodiments, the collar body may have a fluid channel in fluid communication with a hollow interior of the cannula. The fluid channel may be for operatively connecting to a reservoir for containing fluidic media when the first carrier body is in the advanced position to allow fluidic medic to flow from the reservoir to the hollow interior of the cannula.

In further embodiments, the insertion system may include a compliant material. The compliant material may be arranged within the first carrier body to support the piercing member. The compliant material may be for allowing articulation of the piercing member relative to the first carrier body in a case where at least a portion of the piercing member is in the skin of the patient and the piercing member is moved relative to the housing. In yet further embodiments, the piercing member may comprise a needle.

In various embodiments, the driver may comprise a bias member. The bias member may be arranged within the second device housing. The bias member may be for urging the second carrier body toward the advanced position. In some embodiments, the insertion system may include a second driver. The second driver may be arranged within the second device housing to move the first carrier body away from the advanced position to a third position.

In further embodiments, the second driver may comprise a bias member. The bias member may be arranged within the second device housing. The bias member may be for urging the second carrier body toward the third position. In yet further embodiments, the insertion system may include a trigger. The trigger may be for releasably retaining the second carrier body in the advanced position. The trigger may be configured to be operable to release the second carrier body to allow the second carrier body to move to the third position.

In some embodiments, the insertion system may include a trigger. The trigger may be for releasably retaining the second carrier body in the retracted position. The trigger may be configured to be operable to release the second carrier body to allow the second carrier body to move to the advanced position.

In various embodiments, the second carrier body may be configured to operatively connect with at least two different types of piercing members. The second carrier body may be configured to insert at least a portion of a selected one of the at least two different types of piercing members in a case where the selected one of the at least two different types of piercing members is operatively connected to the second carrier body and the second carrier body is moved to the advanced position.

In some embodiments, the second carrier body may be configured to be removable from the selected one of the at least two different types of piercing members and adapted for reuse with another one of the at least two different types of piercing members. In some embodiments, the insertion system may be removable from the selected one of the at least two different types of piercing members. In further embodiments, the insertion system may be completely removable from the selected one of the at least two different types of piercing members.

In some embodiments, the piercing member may be supported by the first carrier body is one of the at least two different types of piercing members. In some embodiments, the selected one of the at least two different types of piercing members may be an insertion needle of an insertion set.

In some embodiments, the selected one of the at least two different types of piercing members may be a lancet for obtaining a fluid sample from the patient. In further embodiments, the insertion system may include a guard. The guard may be configured to be removably attachable to the second device housing. The guard may have an aperture for allowing the lancet to extend through in a case where the lancet is operatively connected to the second carrier body and the second carrier body is moved to the advanced position.

In some embodiments, a distance traveled by the first carrier body relative to the first device housing from the retracted position to the advanced position may be equal to at least a distance required to insert the selected one of the at least two different types of piercing members in the skin of the patient that is at least equal to an implantable length of the selected one of the at least two different types of piercing members.

A method of making an insertion system in accordance with an embodiment of the present invention may include, but is not limited to any one or combination of, (i) adapting a base to be carried by a patient; (ii) configuring a first device housing to be operatively engaged with and disengaged from the base; (iii) arranging a first carrier body for movement within at least a portion of the first device housing at least between a retracted position and an advanced position, the first carrier body for supporting a piercing member in a position orientated for insertion through skin of the patient upon movement of the first carrier body from the retracted position to the advanced position; (iv) configuring a second device housing to be operatively engaged with and disengaged from the first device housing, the second device housing comprising; (v) arranging a second carrier body for movement within at least a portion of the second device housing at least between a retracted position and an advanced position, the second carrier body operatively connectable with the first carrier body; and (vi) arranging a driver within the second device housing to move the first carrier body from the retracted position toward the advanced position to insert at least a portion of the piercing member through skin of the patient.

An insertion system in accordance with an embodiment of the present invention may include, but is not limited to, a housing, a piercing member, and a compliant material. The piercing member may be arranged at least partially within the housing, the piercing member for piercing a membrane. The compliant material may be arranged within the housing to support the piercing member. The compliant material may be for allowing articulation of the piercing member relative to the housing in a case where the piercing member is in the membrane and moved relative to the housing.

In various embodiments, the compliant material may be for allowing articulation of the piercing member relative to the housing in a case where the piercing member is in the membrane and moved laterally relative to the housing.

In various embodiments, the compliant material may be for allowing pivotal movement of the piercing member relative to the housing in a case where the piercing member is in the membrane and moved laterally relative to the housing.

In various embodiments, the compliant material may be adapted to provide a seal between the piercing member and the compliant material to substantially prevent fluidic media from flowing between the compliant material and the piercing member.

In various embodiments, the insertion system may include a seal member. The seal member may be arranged between the compliant material and the piercing member for substantially preventing fluidic media from flowing between the compliant material and the piercing member.

In various embodiments, the compliant material may be adapted to adhere to the piercing member.

In various embodiments, the compliant material may be arranged to support the piercing member such that the piercing member does not contact the housing.

In various embodiments, the piercing member may have a first opening and a second opening. One of the first opening and the second opening may be for receiving fluidic media into a hollow interior of the piercing member. The other of the one of the first opening and the second opening may be for allowing the fluidic media to exit the hollow interior of the needle. The compliant material may be arranged at least partially in between the first opening and the second opening. In some embodiments, the compliant material may be arranged completely between the first opening and the second opening.

In various embodiments, the piercing member may have a first opening and a second opening. One of the first opening and the second opening may be for receiving fluidic media into a hollow interior of the piercing member. The other of the one of the first opening and the second opening may be for allowing the fluidic media to exit the hollow interior of the needle. The compliant material may have a body for supporting the piercing member. The body may have a recess in communication with one of the first opening and the second opening. In some embodiments, the recess may be defined by a surface sloped to correspond generally to an angle of articulation of the piercing member relative to the housing.

In various embodiments, the piercing member may comprise a needle. In various embodiments, the housing may have a fluid channel for alignment with a reservoir. The fluid channel may be in fluid communication with a hollow interior of the piercing member. In various embodiments, the housing may have a chamber for containing the compliant material. At least a portion of the needle may extend through the chamber of the housing.

In various embodiments, the insertion system may include a retaining member. The retaining member may be for retaining the compliant material within the housing. In some embodiments, the retaining member may comprise at least one of a cap, glue joint, and a septum.

In various embodiments, the housing may be made of the compliant material to allow articulation of the piercing member relative to the housing in a case where the piercing member is moved relative to the housing. In various embodiments, the membrane may comprise skin of a patient. The compliant material may be for allowing articulation of the piercing member relative to the housing in a case where the piercing member is in the skin of the patient and moved relative to the housing. In some embodiments, the piercing member may have a hollow interior for conveying fluidic media.

A method of making an insertion system in accordance with an embodiment of the present invention may include, but is not limited to any one or combination of, (i) providing a housing; (ii) arranging a piercing member at least partially within the housing, the piercing member for piercing a membrane; and (iii) arranging a compliant material within the housing to support the piercing member, the compliant material for allowing articulation of the piercing member relative to the housing in a case where the piercing member is in the membrane and moved relative to the housing.

BRIEF DESCRIPTION OF THE DRAWINGS

FIG. 9 illustrates a medical device in accordance with an embodiment of the present invention;

FIG. 10 illustrates a medical device in accordance with an embodiment of the present invention;

DETAILED DESCRIPTION

Figure 1:
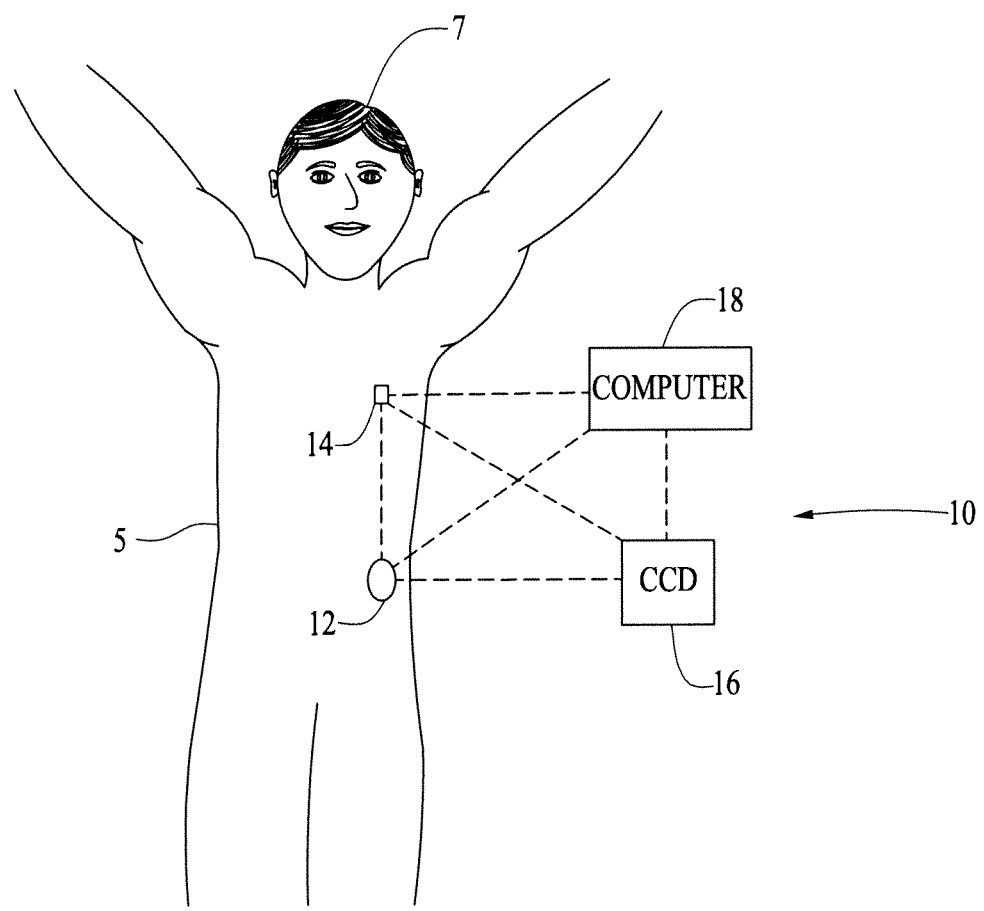
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. Patent Applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; (liii) U.S. patent application Ser. No. 12/360,813, filed Jan. 27, 2009, "Multi-Position Infusion Set Device And Process"; (liv) U.S. Patent Pub. No. US 2007/0142776 (application Ser. No. 10/314,653), filed Dec. 9, 2002, "Insertion Device For An Insertion Set and Methods Of Using The Same." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
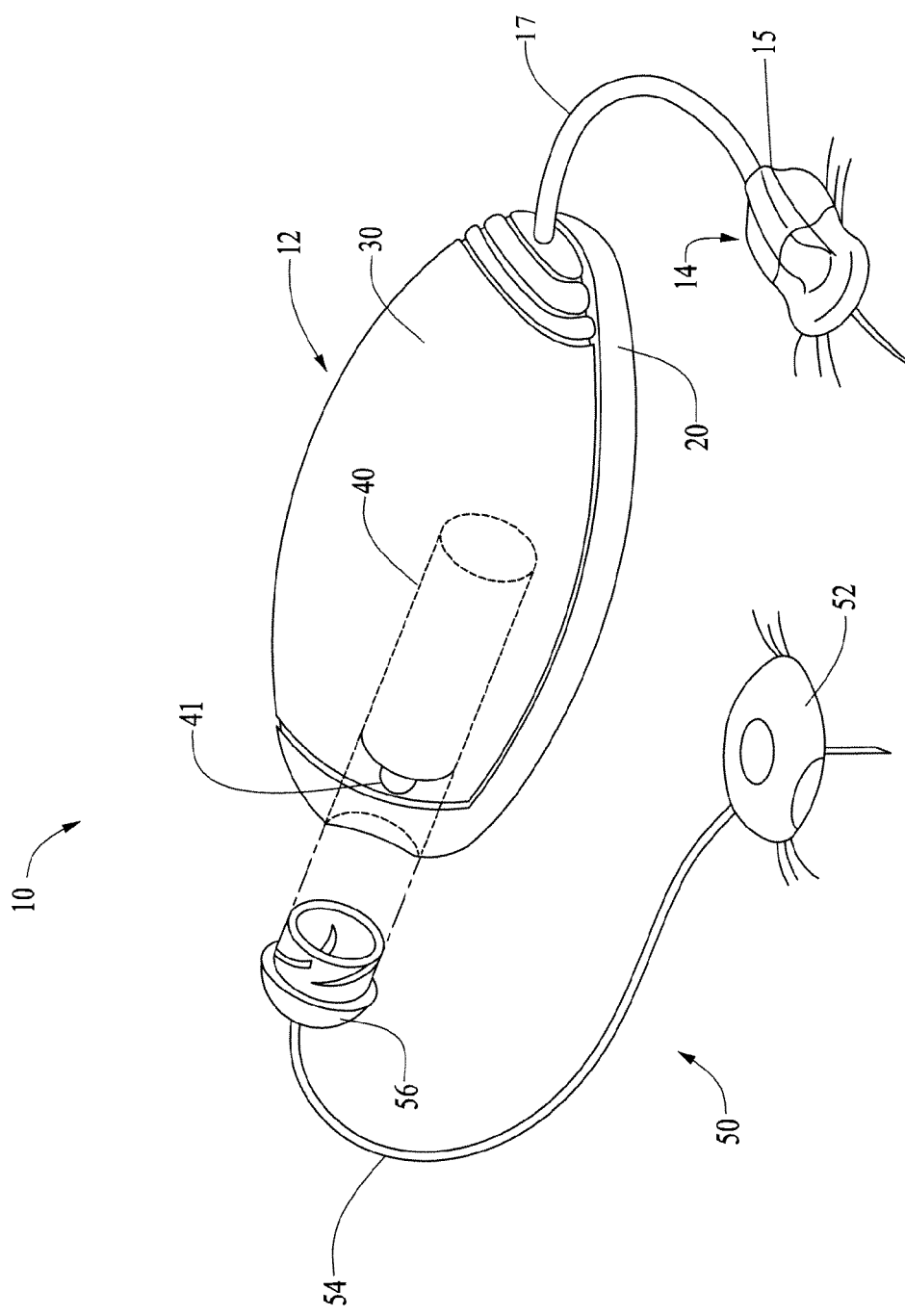
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same," which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
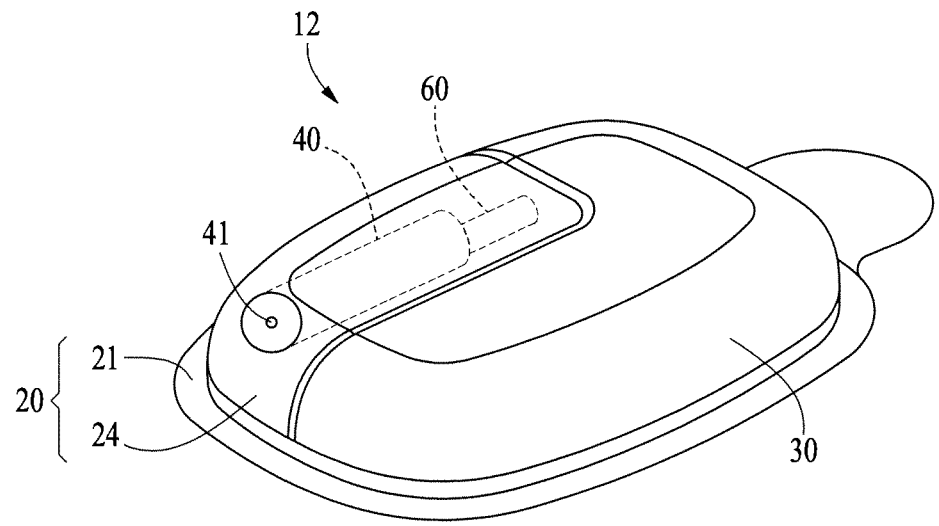
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
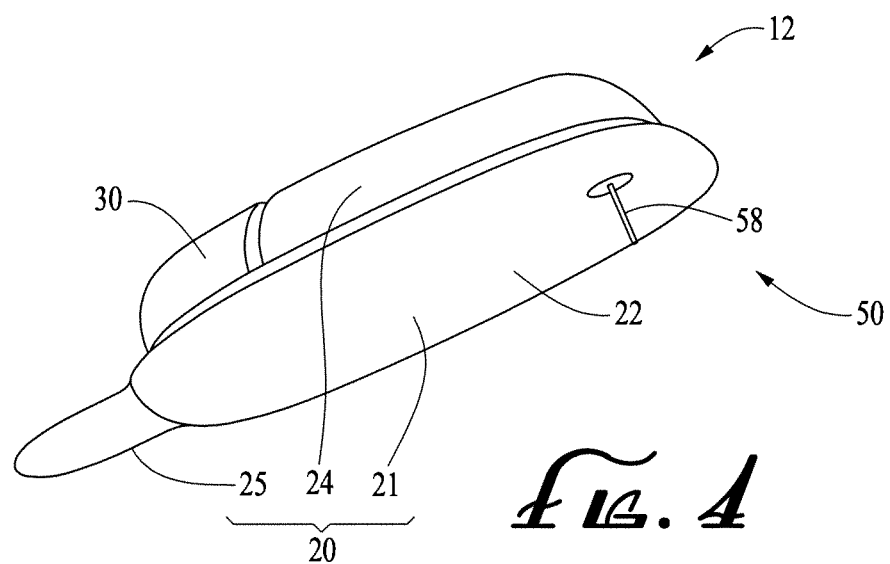
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
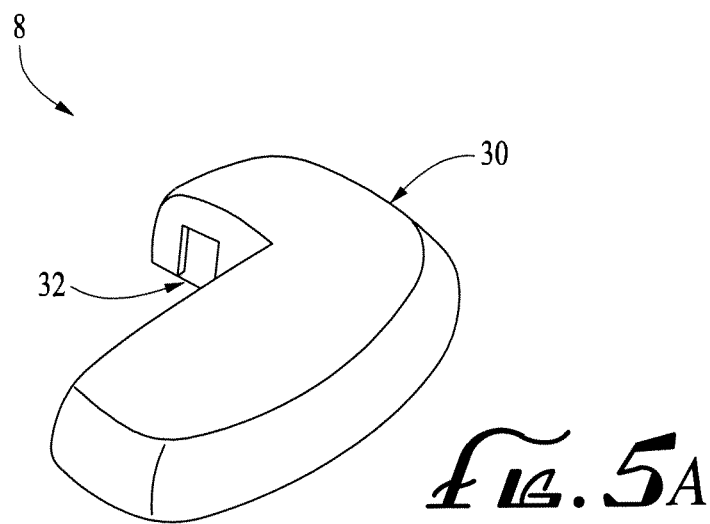
FIG. 5A illustrates a durable portion of a delivery device in accordance with an embodiment of the present invention.
Figure 5B:
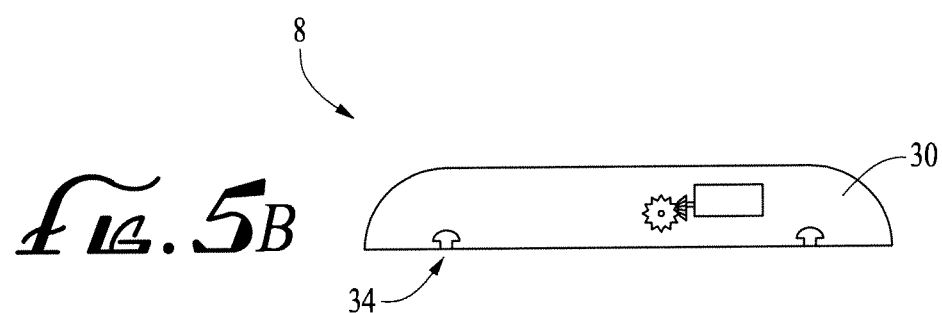
FIG. 5B illustrates a section view of a durable portion of a delivery device in accordance with an embodiment of the present invention.
Figure 5C:
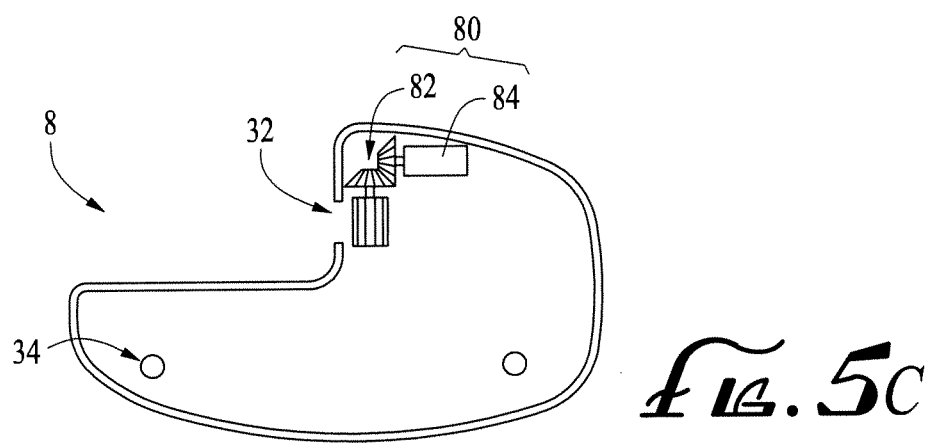
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
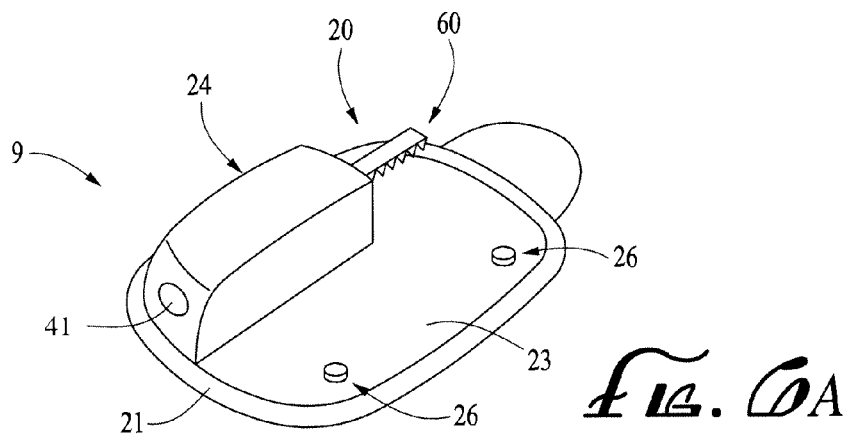
FIG. 6A illustrates a disposable portion of a delivery device in accordance with an embodiment of the present invention.
Figure 6B:
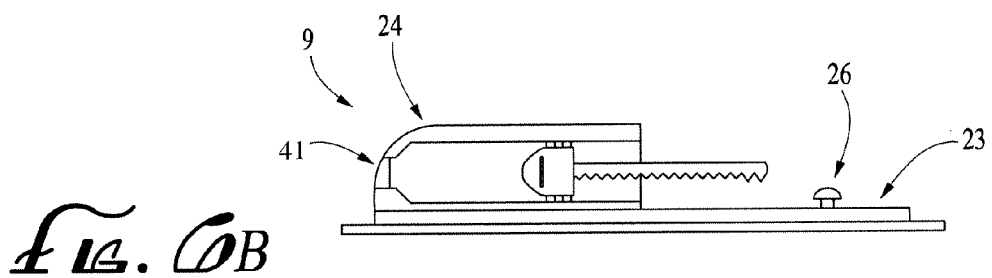
FIG. 6B illustrates a section view of a disposable portion of a delivery device in accordance with an embodiment of the present invention.
Figure 6C:
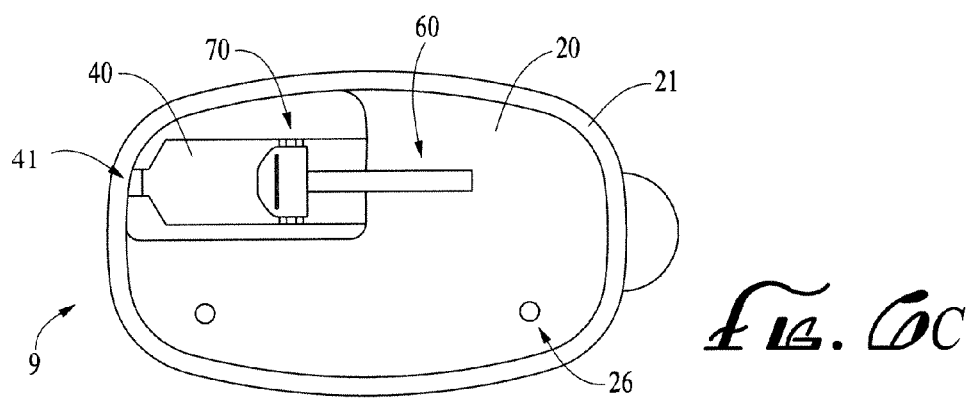
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 may include the reservoir status circuitry (not shown), and the reservoir status circuitry may be configured to read data from the reservoir circuitry (not shown) when the reservoir system 40 is inserted into the disposable portion 9.

In various embodiments, the reservoir status circuitry (not shown) may be further configured to store data to the reservoir circuitry after at least some of the contents of the reservoir system 40 have been transferred out of the reservoir system 40 to update information in the reservoir circuitry (not shown)

related to an amount of contents still remaining in the reservoir system 40. In some embodiments, the reservoir status circuitry (not shown) may be configured to store data to the reservoir circuitry (not shown) to update information in the reservoir circuitry (not shown) related to an amount of contents remaining in the reservoir system 40 when the reservoir system 40 is inserted into the disposable portion 9. In some embodiments, the delivery device 12 may include the reservoir status circuitry (not shown) and the reservoir system 40 may include the reservoir circuitry (not shown), and the reservoir status circuitry (not shown) may selectively inhibit use of the delivery device 12 or may selectively provide a warning signal based on information read by the reservoir status circuitry (not shown) from the reservoir circuitry (not shown).

Aspects of the present invention relate, generally, to needle inserter or inserting devices and methods and medical devices, such as, but not limited to sensors, monitors and infusion medium delivery systems, devices and methods that include such needle-inserting devices and methods. The needle-inserting device and method may operate to insert a needle or cannula through skin of a user-patient, for example, to provide a fluid flow path for conveying an infusion medium through a hollow channel in the needle or cannula and into the user-patient and/or to convey a fluid from the user-patient to one or more sensor elements. Embodiments of the present invention may be configured, as described herein, to provide a reliable, cost effective, and easy-to-use mechanism for inserting a needle or cannula to a specific depth into a user-patient with minimal traumatic effect.

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation.

Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

The structures and methods described with respect to FIGS. 7-16 and 17-26 may be employed in any suitable device or system in which two members that, at some period of time, are not connected in fluid flow communication, are to be connected together in a manner that allows fluid to flow from one member to the other. In one example embodiment, the structure and method is described with respect to a first member including a fluid reservoir for containing an infusion medium that may be connectable to a second member including an injection site structure in which a hollow needle or cannula is or may be inserted into a user-patient, for conveying fluid media to the user-patient. However, a connection structure according to embodiments of the present invention may be employed to connect any two (or more) members together for fluid flow communication with each other.

In FIGS. 7-12, an example of a structure 100 and method for connecting two members in fluid flow communication is described with reference to a first member 102 and a second member 103. The first member 102 may include a housing 104 on a base 106. The housing 104 may be formed integral with the base 106 or may be formed as a separate structure connected to the base 106 in a fixed relation to the base 106. The housing 104 and the base 106 each may be made of any suitably rigid material, including, but not limited to plastic, metal, ceramic, composite material, or the like.

The housing 104 may include an injection site section 105 containing an injection site structure in which a hollow needle or cannula may be inserted into a user-patient for conveying fluidic media to or from the user-patient. The housing 104 may be made of a material of suitable strength and durability such as, but not limited to, plastic, metal, glass, or the like. In other embodiments, instead of or in addition to an injection site, the housing 104 may contain, be part of, or be operatively connected to any other suitable structure for conveying, containing, and/or processing fluidic media.

The second member 103 may also include a housing 108, which in the illustrated embodiment may include a reservoir 107 for containing fluidic media. The reservoir 107 may be configured and/or made of materials as previously described with respect to reservoir system 40 (e.g., FIGS. 1-6C). The second member 103 may be held within or otherwise be covered by an outer housing 109 configured to attach to the base 106. The outer housing 109 may be configured to connect to the base 106 of the first member 102 by any suitable connection structure.

In particular embodiments, at least one of the outer housing 109 and the base 106 may include one or more flexible pawls, protrusions, indentations, or the like for engaging and/or receiving one or more corresponding pawls, protrusions, indentations, or the like on the other of the base 106 and the outer housing 109 to provide a suitable connection structure. Alternatively or in addition, the connection structure may include adhesive material or other suitable connectors.

In other embodiments, the housing 108 may be or be connected to a sensor housing (not shown) containing sensor components. In yet other embodiments, the housing 108 may contain, be part of, or be operatively connected to any other suitable structure for conveying, containing, and/or processing fluidic media. The housing 108 may be made of any suitably rigid material, including, but not limited to, plastic, metal, ceramic, composite material, or the like.

The housing 104 may have or be connected to a receptacle structure 110. The receptacle structure 110 may have an opening 112 leading into a chamber 114 within the receptacle structure 110. In some embodiments, the receptacle structure 110 may be part of the housing 104 adjacent a section of the housing 104 containing the injection site section 105. In other embodiments, the receptacle structure 110 may include a further housing connected to the housing 104.

The receptacle structure 110 may include a first septum 116 located within the chamber 114 and may be moveable within the chamber 114 toward and away from the opening 112. The receptacle structure 110 may also include a bias mechanism 118, which may apply a bias force on the first septum 116 in a direction toward the opening 112. The bias mechanism 118 may be arranged for forcing the first septum 116 against the opening 112. One or more annular protrusions or one or more appropriately shaped or positioned protrusions 120 adjacent the opening 112 may be provided to inhibit the first septum 116 from being forced out of the chamber 114 through the opening 112 by the force of the bias mechanism 118.

The first septum 116 may have a front surface 116a that is at least partially exposed through the opening 112 when the first septum 116 is urged against the opening 112 by the bias mechanism 118. The first septum 116 may have a back surface 116b facing toward an interior of the chamber 114. The first septum 116 may be made of any suitable material that may be pierceable by a needle, such as, but not limited to, a natural or synthetic rubber material, silicon, or the like. In some embodiments, the first septum 116 may be made of a self-sealing material capable of sealing itself after a needle has pierced the first septum 116 and was subsequently withdrawn from the first septum 116.

In some embodiments, the bias mechanism 118 may be a coil spring located within the chamber 114 on an opposite side of the first septum 116 with respect to the front surface 116a. In other embodiments, the bias mechanism 118 may be provided in any suitable manner for biasing the first septum 116 toward the opening 112. These may include, but are not limited to, other types of springs, pressurized fluid within the chamber 114, a collapsible skirt structure extending from the first septum 116 with a natural or built-in spring force, chemical, substance that expands upon contact with another chemical or substance, or upon application of energy from an energy source such as a heat, laser, or other radiation source, or the like. For example, in some embodiments, the first septum 116 may have a flexible accordion-like configuration to allow expansion and contraction of the skirt structure.

A needle 124 may be supported within the chamber 114. The needle 124 may be hollow and may have a sharp end 124a directed toward the back surface 116b of the first septum 116. In some embodiments, the needle 124 may be supported within the bias mechanism 118 such that a longitudinal axial dimension of the needle 124 extends generally parallel to a longitudinal axial dimension of the bias mechanism 118.

The needle 124 may be supported by a supporting structure located within the receptacle structure 110. In some embodiments, the supporting structure may be a wall integral with the receptacle structure 110. The supporting structure may be located, for example, on an opposite end of the chamber 114 relative to the end of the chamber 114 at which the opening 112 is located. In other embodiments, the supporting structure may be any suitable structure that is generally fixed relative to the receptacle structure 110 and is able to support the needle 124 in a generally fixed relation to the receptacle structure 110.

The needle 124 may be made of any suitably rigid material, including, but not limited to metal, plastic, ceramic, or the like, and may have a hollow channel extending in a lengthwise dimension of the needle 124. The hollow channel in the needle 124 may be open on the sharp end 124a of the needle 124 and may be open at another location 124b along the lengthwise dimension of the needle 124, such as, but not limited to, the needle end opposite the sharp end 124a. The hollow channel in the needle 124 may provide a fluid flow path between the sharp end 124a of the needle 124 and the opening 124b of the needle 124. In some embodiments, the opening 124b of the needle 124 may be connected in fluid flow communication with a manifold 128 in the injection site section 105.

The housing 108 of the second member 103 may include a connection portion 130 having a hollow interior chamber 132 and an opening 134 into the interior chamber 132. A second septum 136 may be supported by the housing 108 to seal the opening 134. The second septum 136 may be supported in a fixed relation to the housing 108, for example, within the housing 108 at one end of the interior chamber 132.

Figure 7:
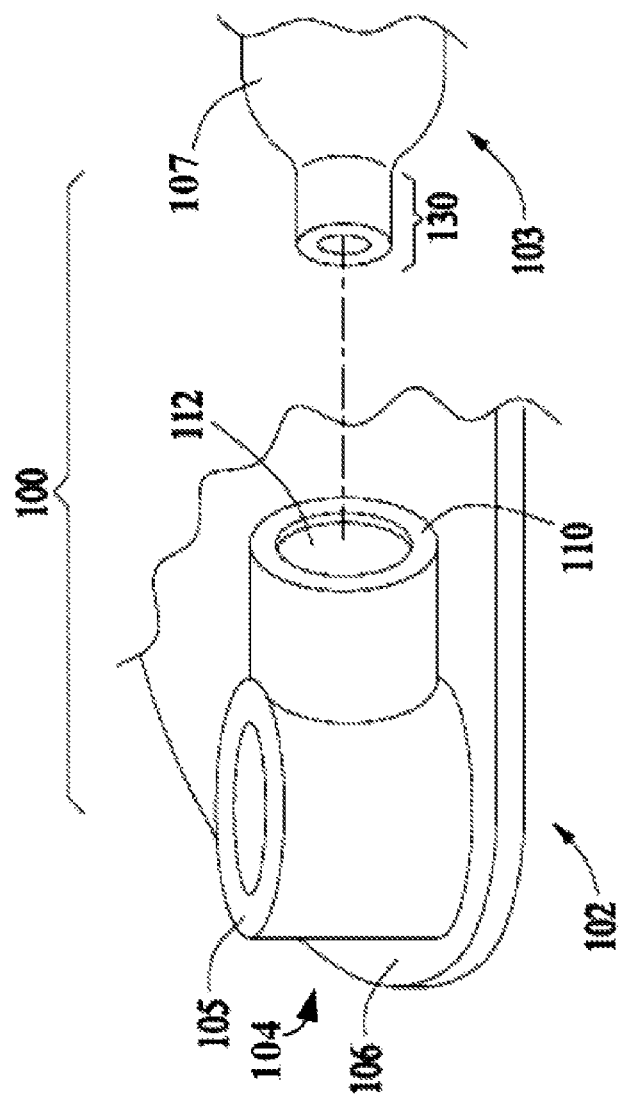
FIG. 7 illustrates portions of a medical device in accordance with an embodiment of the present invention.
Figure 8:
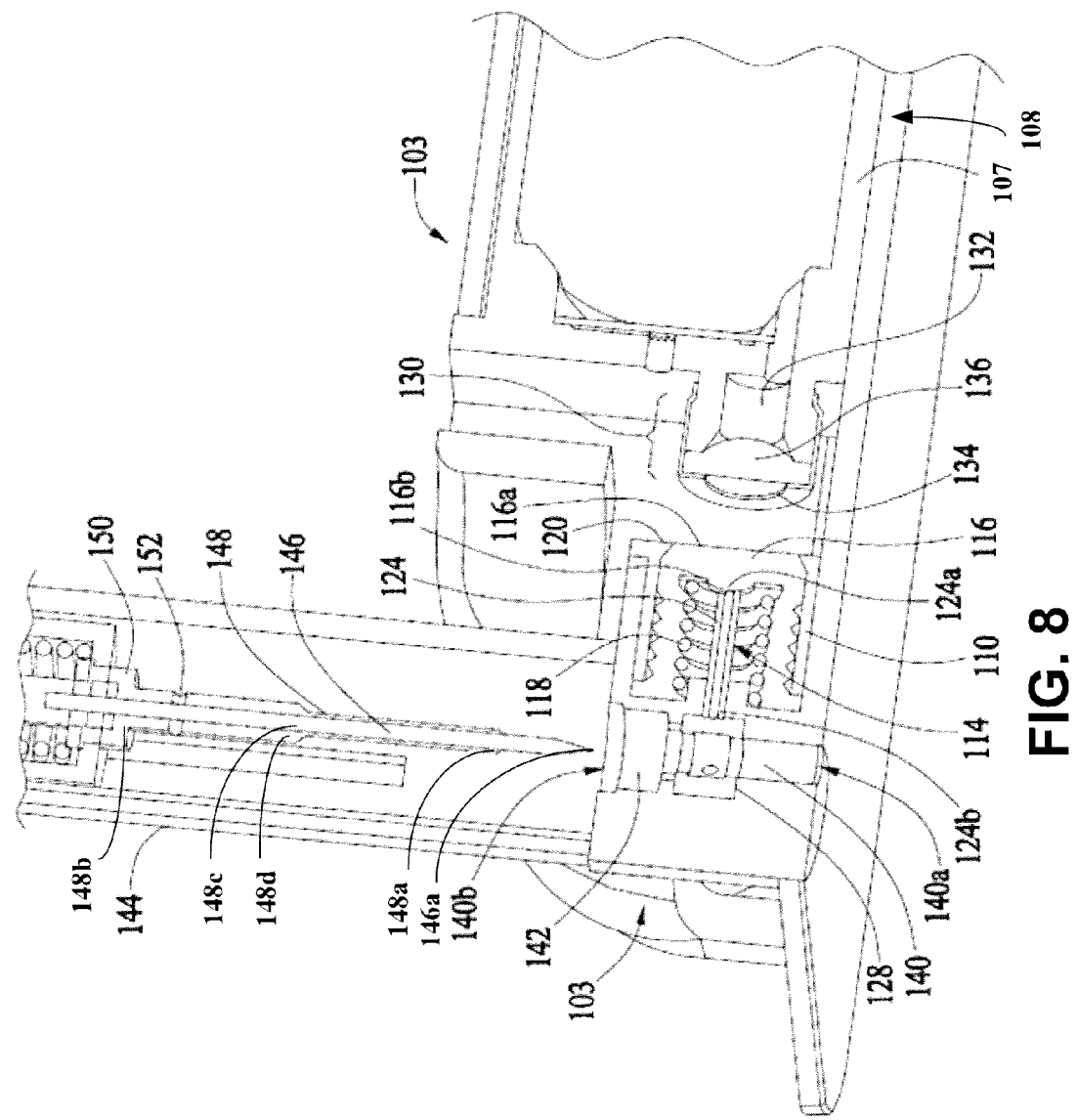
FIG. 8 illustrates a medical device in accordance with an embodiment of the present invention.
Figure 11:
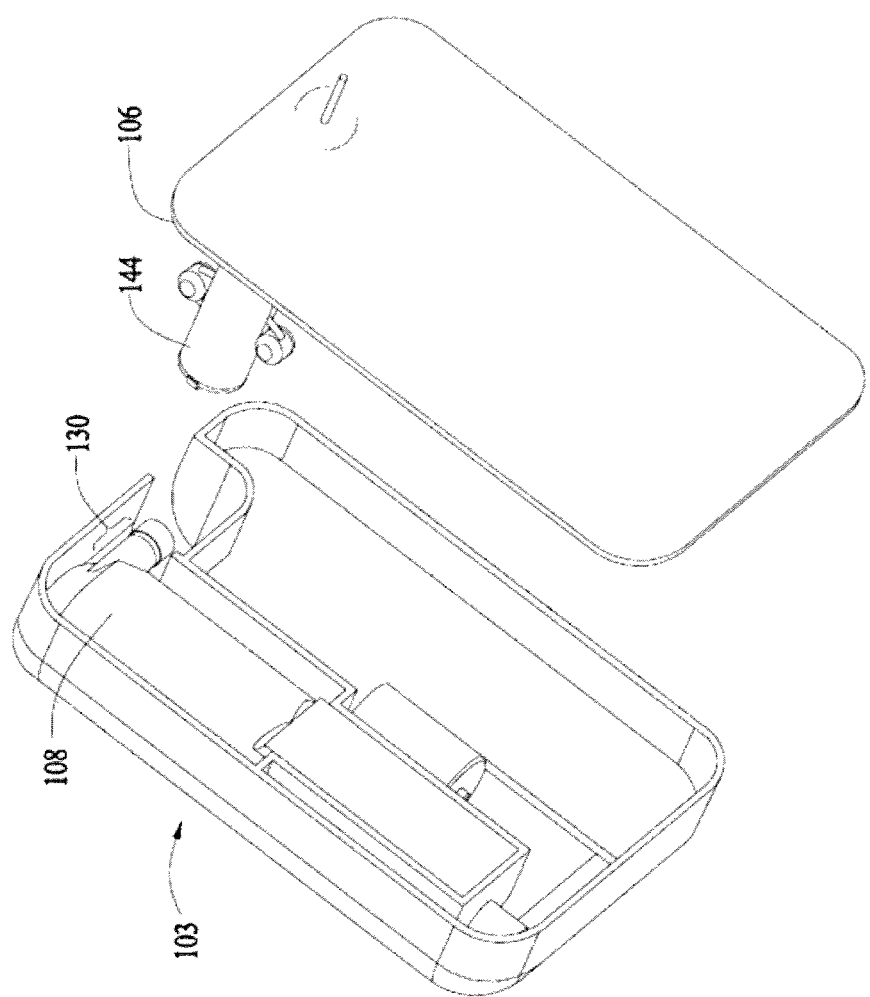
FIG. 11 illustrates a medical device in accordance with an embodiment of the present invention.
Figure 12:
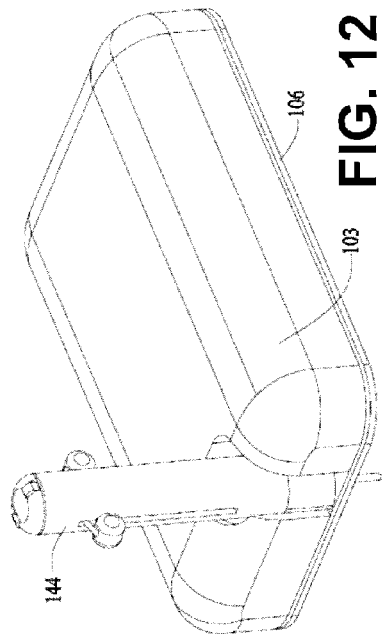
FIG. 12 illustrates a medical device in accordance with an embodiment of the present invention.

The connection portion 130 of the housing 108 may have a suitable shape and size to fit at least partially within the opening 112 of the receptacle structure 110 in the first member 102 when the first member 102 and the second member 103 are connected together. In the drawings of FIGS. 7 and 8, the first member 102 and the second member 103 are shown in a separated, disconnected relation, wherein the connection portion 130 of the housing 108 is outside of the opening 112 of the receptacle structure 110. By moving the first member 102 and the second member 103 together to insert the connection portion 130 into the opening 112 of the housing 108 an end surface of the connection portion 130 may be urged against the first septum 116. This may cause the moveable first septum 116 to move relative to the housing 108 against the force of the bias mechanism 118 toward the interior of the chamber 114. As the first septum 116 is moved toward the interior of the housing 108, the sharp end 124a of the needle 124 may pierce the first septum 116. Continued relative movement of the first member 102 and the second member 103 together may cause the sharp end 124a of the needle 124 to pass through the first septum 116 in the first member 102, then pierce, and pass through the second septum 136 in the second member 103.

When the first member 102 and the second member 103 are brought together (e.g., FIG. 9), at least a portion of the connection portion 130 may extend inside of the receptacle structure 110. With reference to FIGS. 8 and 9, the needle 124 may pierce the first septum 116 and the second septum 136 to form a fluid flow path between the interior chamber 132 of the connection portion 130 and the manifold 128 or other structure at the opening 124b of the needle 124. The receptacle structure 110 and the connection portion 130 may be provided with mating connectors that provide, for example, a snap or friction connection upon the first member 102 and the second member 103 being brought together as shown in FIG. 9. In some embodiments, the mating connectors may include a protrusion (not shown) on one or the other of the receptacle structure 110 and the connection portion 130. The other of the receptacle structure 110 and the connection portion 130 may include a groove or indentation (not shown) arranged to engage each other in a snap-fitting manner upon the connection portion 130 being extended into the receptacle structure 110 a suitable distance.

As mentioned above, in some embodiments, the opening 124b of the needle 124 may be connected in fluid flow communication with the manifold 128 in the injection site section 105. The injection site section 105 may include a channel 140 extending through the housing 104 and the base 106. The channel 140 may have an open end 140a on a bottom surface (relative to the orientation shown in FIG. 8) of the base 106. The channel 140 may have another open end 140b at an upper surface (relative to the orientation shown in FIG. 8) of the injection site section 105 of the housing 104.

The manifold 128 may be located along a length of the channel 140 and may be in fluid flow communication with the channel 140. Accordingly, the needle 124 may be arranged in fluid flow communication with the interior of the channel 140 through the manifold 128. The channel 140 may include a channel section 142 having a larger radial dimension relative to a remaining portion of the channel 140 and may have a suitable shape and size to receive a needle and/or cannula, as will be described later. The manifold 128 may be made of a material of suitable strength and durability such as, but not limited to, plastic, metal, glass, or the like.

A needle-inserting device 144 may be located adjacent the open end 140b of the channel 140 and arranged to selectively extend a needle and/or cannula into the open end 140b of the channel 140 and at least partially through the channel 140 as will be described. In various embodiments, the needle-inserting device 144 may be configured to be integral with or otherwise fixed to the section 105 of the housing 104 of the first member 102. In other embodiments, the needle-inserting device 144 may be a separate device from the housing 104 and may be selectively engaged or connected to, for example in alignment with the channel 140 (e.g., FIG. 8), and disengaged or disconnected from the injection site section 105 of the housing 104.

In embodiments in which the needle-inserting device 144 is a separate structure that connects to and disconnects from the injection site section 105, a suitable connection structure may be provided on the needle-inserting device 144 and/or the injection site section 105 to provide a manually releasable connection between those components. For example, the connection structure may include, but is not limited to, a threaded extension on one or the other of the needle-inserting device 144 and the injection site section 105 and a corresponding threaded receptacle on the other of the injection site section 105 and the needle-inserting device 144 for receiving and mating with the threaded extension in threaded engagement. In other embodiments, other suitable connection structures may be employed, including, but not limited to, flexible pawls or extensions on one or the other of the needle-inserting device 144 and the injection site section 105 and a corresponding aperture, stop surface, or the like on the other of the other of the injection site section 105 and the needle-inserting device 144 or friction fitting engageable portions on each of the section 105 and needle-inserting device 144.

In the drawing of FIG. 8, the needle-inserting device 144 is shown as connected to the injection site section 105 with a needle 146 and a cannula 148 in a retracted state. With reference to FIGS. 7-16, the needle-inserting device 144 may be operated to selectively move the needle 146 and the cannula 148 from the retracted state (e.g., FIG. 8) to an extended state (e.g., FIG. 13) in which the needle 146 and the cannula 148 extend through the opening 140b of the channel 140 and at least partially through the channel 140 such that a sharp end 146a of the needle 146 and at least a portion of the length of the cannula 148 extend out the opening 140a of the channel 140.

Various examples of suitable structures for needle-inserting devices are described in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various needle-inserting devices are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method,", all of which are herein incorporated by reference in its entirety. Other examples of suitable structures for needle-inserting devices are described herein.

The cannula 148 may have a hollow central channel 148c extending along a longitudinal length of the cannula 148 and open at one end 148a that may be adjacent the sharp end 146a of the needle 146. An end 148b of the cannula 148 opposite the open end 148a may have a head 150 having a larger radial dimension than a shaft portion 148d of the cannula 148. The cannula head 150 may have a suitable shape and size to fit into the channel section 142 of the channel 140 when the needle 146 and the cannula 148 are moved to the extended state by the needle-inserting device 144.

In particular embodiments, the cannula head 150 may include one or more protrusions and/or indentations for engaging one or more corresponding indentations and/or protrusions in the channel section 142 of the injection site section 105 to provide a friction fit, snap fit, or the like. Accordingly, the cannula 148 may be locked or retained within the injection site section 105 upon the needle 146 and cannula 148 being moved to the extended state by the needle-inserting device 144. In further embodiments, instead of or in addition to engaging protrusions and indentations, one or more other mechanical structures may be employed to provide a suitable retaining function for retaining the cannula 148 in place within the injection site section 105, including, but not limited to, a friction fit structure, snap fit, or the like.

The cannula 148 may have a connection channel 152 provided in fluid flow communication with the hollow central channel 148c of the cannula 148. The connection channel 152 may be provided along the longitudinal length of the cannula 148 at a location at which the connection channel 152 aligns with the manifold 128 (i.e., in fluid flow communication with an interior of the manifold 128) when the needle 146 and the cannula 148 have been moved to the extended state by the needle-inserting device 144. In this manner, upon the cannula 148 being moved to the extended state, the hollow central channel 148c of the cannula 148 may be arranged in fluid flow communication with the reservoir 108 through the manifold 128 and the connection channel 152.

Thus, according to some embodiments, in operation, a first member 102, which may include, for example, a housing 104 having a receptacle 110 and an injection site section 105, may be coupled together with a second member 103, which may include, for example, a housing 108 having a reservoir 107. The first member 102 may be coupled or otherwise operatively connected, by inserting a connection portion 130 of the second member 103 into a receptacle 110 of the first member 102. Upon coupling the first member 102 and the second member 103, fluid flow communication may be provided between the second member 103 and the injection site section 105 in the first member 102.

In various embodiments, the needle-inserting device 144 may be coupled to the injection site section 105 of the housing 104 of the first member 102 or may be provided as part of a single, unitary structure (i.e., integral) with the injection site section 105 of the housing 104. In some embodiments, the base 106 of the first member 102 may be secured to skin of a user-patient at a suitable injection location with, for example, but not limited to, adhesive material as described in U.S. patent application Ser. No. 11/645,435, filed Dec. 26, 2006, entitled "Infusion Medium Delivery system, Device And Method With Needle Inserter And Needle Inserter Device And Method," and/or as described herein. Alternatively or in addition, the base 106 may be secured to the user-patient by one or more other suitable structures, including, but not limited to, straps, or the like.

Once the base 106 is suitably secured to the skin of the user-patient at a suitable injection location, the inserting device 144 may be actuated to move the needle 146 and the cannula 148 from a retracted state (e.g., FIG. 8) to an extended state. In the extended state, the needle 146 and/or the cannula 148 may pierce the skin of the user-patient adjacent the base 106. The cannula 148 may be locked into its extended state by engagement of the cannula head 150 and the channel section 142, as previously described.

With the cannula 148 locked in the extended state, the needle 146 may be retracted, for example, by automatic operation of the needle-inserting device 144 and/or by manual removal of the needle-inserting device 144 from the injection site section 105. Once the needle 146 is removed, the cannula 148 may be held in place by the injection site section 105 with a portion of the cannula 148 extending into the user-patient. As such, the cannula 148 may be connected in fluid-flow communication with the needle 124. Accordingly, by connecting the first member 102 and the second member 103, as described above, then a fluid-flow connection may be provided from the reservoir 107 to the cannula 148 through the needle 124 and the manifold 128.

A connection sequence (e.g., the sequence of connecting the needle-inserting device 144 to the injection site section 105 of the housing 104, connecting the receptacle 110 of the housing 104 to the connection portion 130 of the housing 108 having the reservoir 107, and connecting the base 106 of the first member 102 to the skin of the user-patient) for connecting various components may be different for different embodiments. In some embodiments, the user-patient may be provided with a first member 102 having a base 106, a housing 104, and an injection site section 105 in a pre-connected state with the needle-inserting device 144. In this manner, a user-patient need not have to connect the needle-inserting device 144 to the housing 104 as those parts are supplied to the user in a pre-connected state, for example, from a manufacturing or assembly facility. In such embodiments, the base 106 of the first member 102 may be secured to skin of the user-patient at a suitable injection location. After securing the base 106 to the skin of the user-patient, the needle-inserting device 144 may be activated to cause the needle 146 and the cannula 148 to be moved to the extended state and pierce the skin of the user-patient.

After activation of the needle-inserting device 144, the needle-inserting device 144 may be removed from the injection site section 105, thus leaving the cannula 148 in place within the injection site section 105 and partially extended into the user-patient. With the base 106 of the first member 102 secured to the skin of the user-patient and the cannula 148 inserted at least partially into the user-patient and arranged in fluid-flow communication with the needle 124, the second member 103 may be connected to the first member 102. In particular, the connection portion 130 of the housing 108 of the second member 103 may be inserted into the receptacle 110 of the housing 104 of the first member 102 to provide a fluid-flow connection between the interior of the housing 108 and the needle 124 and, thus, the cannula 148. Accordingly, the housing 108, which may include the reservoir 107, for example, may be coupled in fluid-flow communication with the cannula 148 that has been extended into the user-patient for delivering fluid from the reservoir 107 to the user-patient. In other embodiments, such a connection may be for conveying fluid from the user-patient to the reservoir 107.

While the connection sequence in some of the above embodiments involve securing the base 106 of the first member 102 to the user-patient prior to connection of the second member 103 to the first member 102, in other embodiments, the second member 103 may be connected to the first member 102, as described above, prior to securing the base 106 of the first member 102 onto the skin of the user-patient. In such embodiments, the first member 102 and the second member 103 may be connected together and, thereafter, may be secured to the user-patient, for example, by adhering one or both of the first member 102 and the second member 103 to the skin of the user-patient. In addition, while the connection sequence in the above embodiments involve activating the needle-inserting device 144 prior to the connection of the second member 103 to the first member 102, in other embodiments, the second member 103 may be connected to the first member 102, as described above, prior to activating the needle-inserting device 144.

In some embodiments, such as the embodiments shown in FIGS. 7 and 8, the receptacle 110 may be in the first member 102 and the connection portion 130 may be in the second member 103. In other embodiments, the receptacle 110 may be in the second member 103, for example, in or associated with a housing for a reservoir and the connection portion 130 may be in the first member 102, for example, in or associated with a housing containing an injection site structure.

In some embodiments, such as the embodiments shown in FIGS. 7 and 8, the receptacle 110 may be arranged to allow the connection portion 130 of the second member 103 to be inserted in a direction substantially parallel to a plane of an upper-facing (in the orientation of FIG. 7) surface of the base 106. For example, in the orientation of FIG. 7, the direction of insertion is shown as a horizontal direction of relative motion between the first member 102 and the second member 103.

Again referring to FIGS. 7 and 8, in other embodiments, the receptacle 110 may be arranged in other suitable orientations, including, but not limited to, an orientation allowing an insertion direction (i.e., relative motion of the first member 102 and the second member 103) to be substantially perpendicular to the plane of the upper-facing surface of the base 106. In yet other embodiments, the receptacle 110 may be arranged to allow any other suitable insertion direction at a non-perpendicular angle transverse to the plane of the upper-facing surface of the base 106.

Figure 13:
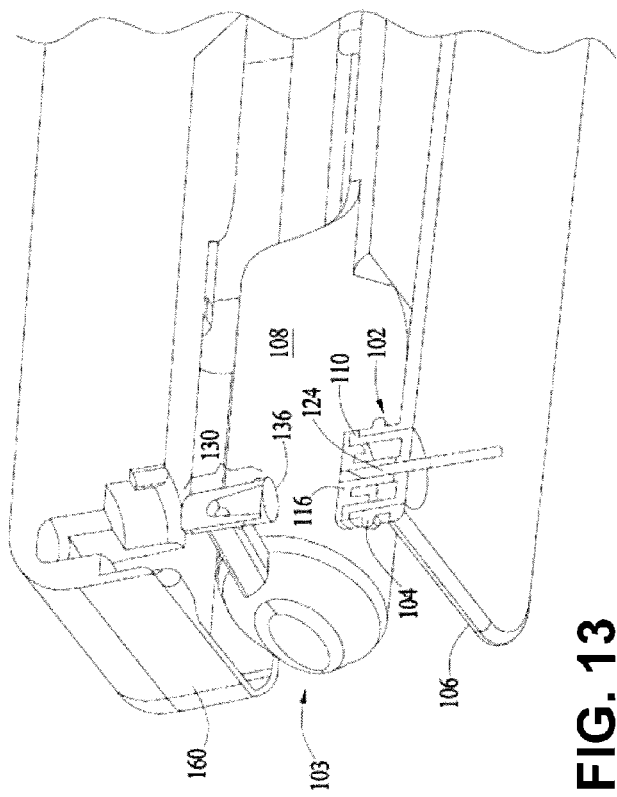
FIG. 13 illustrates a medical device in accordance with an embodiment of the present invention.
Figure 14:
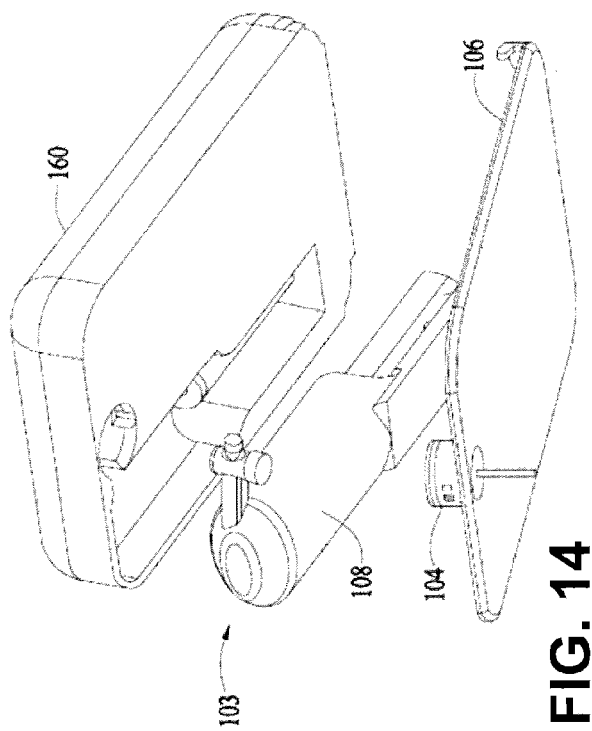
FIG. 14 illustrates a medical device in accordance with an embodiment of the present invention.

An example arrangement shown in FIGS. 13-16 provides an insertion direction (i.e., relative motion of the first member 102 and the second member 103) that may be substantially perpendicular to the plane of the upper-facing (in the orientation of FIG. 8) surface of the base 106. Components in FIGS. 13-16 are identified by reference numbers that are the same as reference numbers used in FIGS. 7-12 for components having similar structure and function. In FIGS. 13 and 14, the injection site section 105 in the housing 104 is shown in a state after a needle-inserting device has been operated to move a cannula 148 to the extended position.

Figure 15:
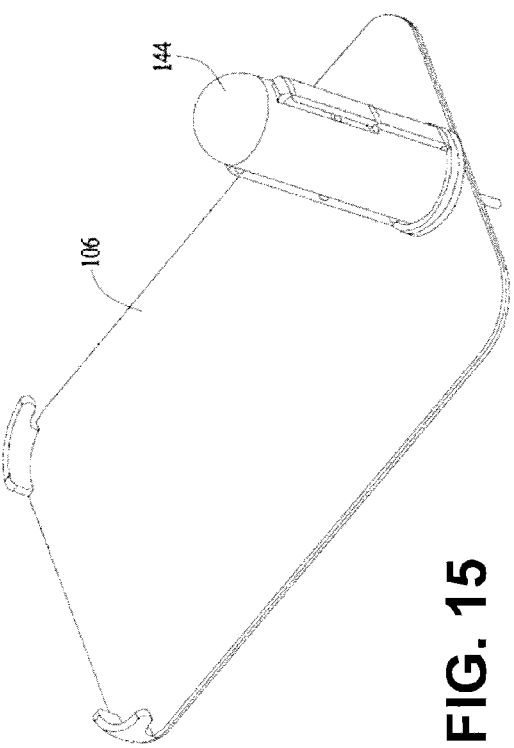
FIG. 15 illustrates a medical device in accordance with an embodiment of the present invention.
Figure 16:
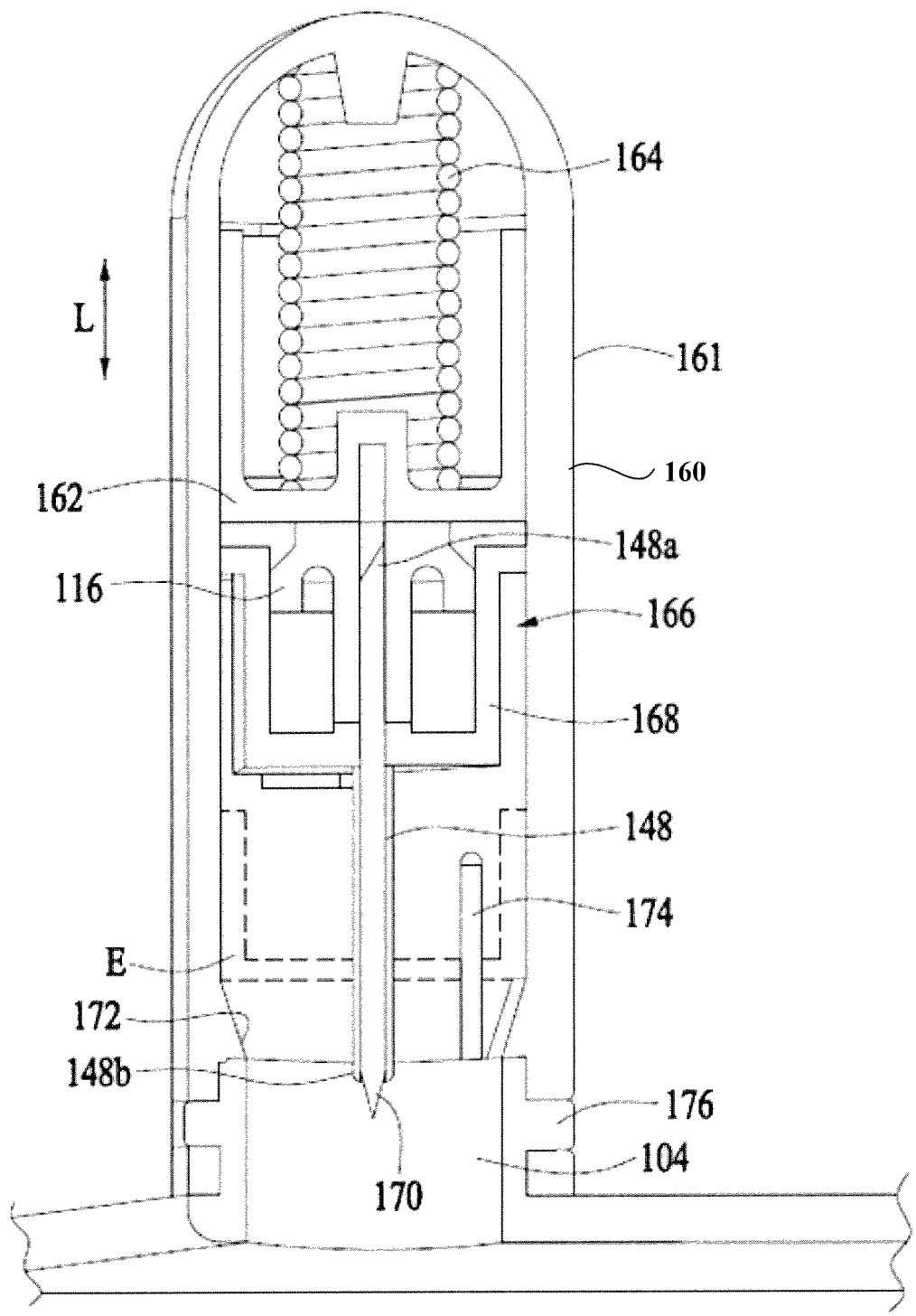
FIG. 16 illustrates cross-section of a needle-inserting device in accordance with an embodiment of the present invention.
Figure 17:
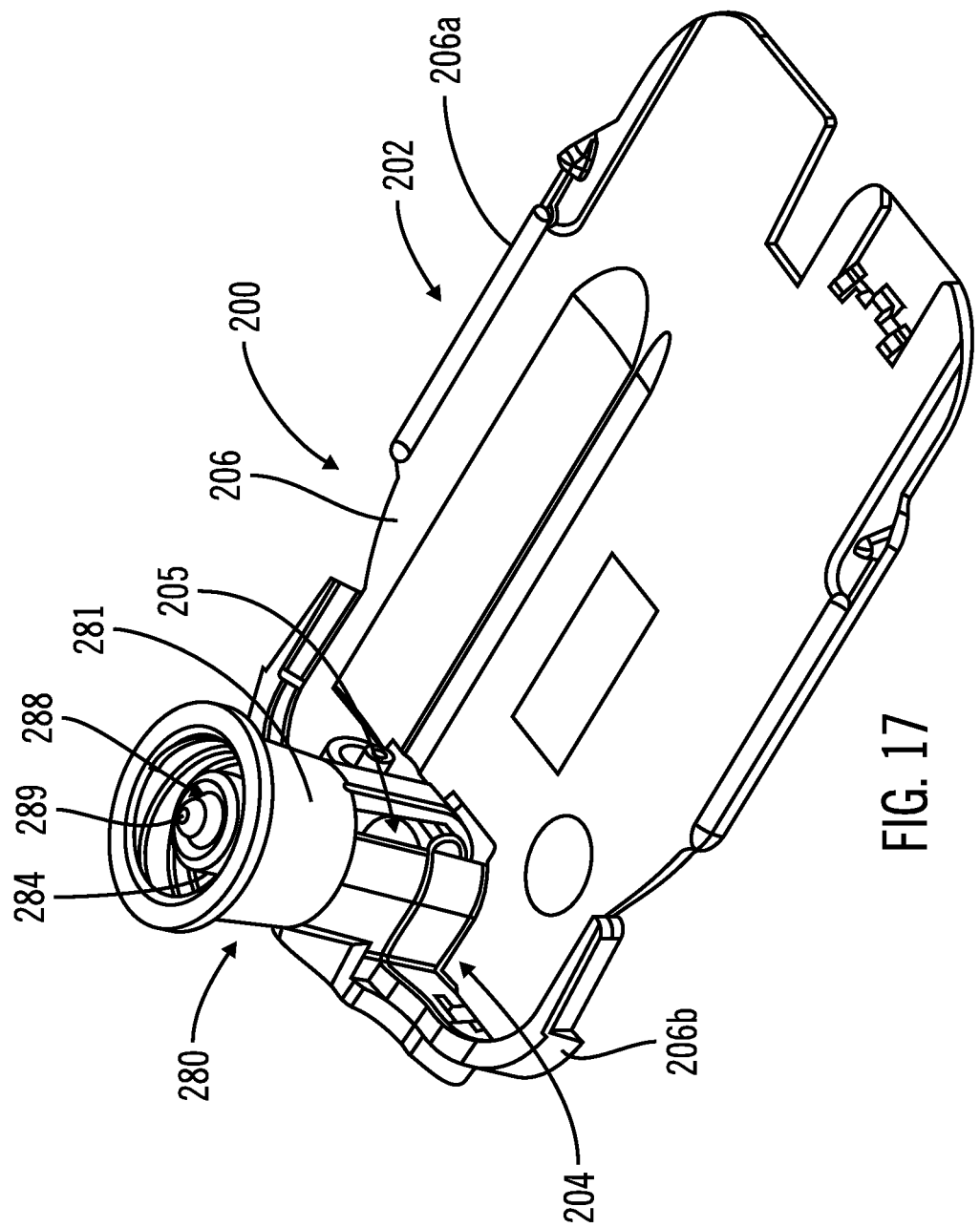
FIG. 17 illustrates a medial device in accordance with an embodiment of the present invention.

FIGS. 15 and 16 show the base 106 of the first member 102 (of the embodiment of FIGS. 13 and 14) with a needle-inserting device 144 attached to the housing 104. The needle-inserting device 144 may include a housing 160 adapted to be securable to the base 106 in any suitable manner, such as, but not limited to the manners of connecting a needle-inserting device 144 to the injection site structure 105 discussed above with respect to the embodiment of FIGS. 7-12. Returning to FIGS. 15 and 16, the housing 160 may contain an internal chamber having a longitudinal dimension L and a moveable plunger 162 located within the housing 160 and moveable along the longitudinal dimension L from a retracted position (shown in solid lines in FIG. 16) to an extended position (in which the plunger 162 is moved to a position E shown in broken lines in FIG. 16).

A bias member 164, such as, but not limited to, a coil spring arranged within the housing 160 may be configured to impart a bias force on the plunger 162 when the plunger 162 is in the retracted position to urge the plunger 162 toward the extended position E. A locking mechanism (not shown) may be provided such as, but not limited to, a manually moveable projection, lever, slider, or the like, connected to or extending through the housing 160 and engages the plunger 162 or other structure holding the plunger 162 in a releasable manner to selectively hold the plunger 162 in its retracted state against the bias force of the bias member 164 and to allow a user-patient to selectively release the plunger 162 to move in the longitudinal direction L under the force of the bias member 164.

An insert structure 166 may be arranged within the housing 160 for movement in the longitudinal direction L by action of movement of the plunger 162. The insert structure 166 may include, for example, a cup-shaped body 168. The cup-shaped body 168 may be made of a material of suitable strength and durability such as, but not limited to, plastic, metal, glass, or the like. The cup-shaped body 168 may hold a first septum 116. The septum 116 may be made of a material such as silicone, rubber, plastic, a resealable membrane, or the like.

A hollow cannula 148 may have one open end 148*a* and a sharp tip arranged adjacent the first septum 116 or at least partially within the first septum 116. The hollow cannula 148 may extend through the cup-shaped body 168 and may have a second open end 148*b*. The hollow cannula 148 may be fixed to the cup-shaped body 168 to move with movement of the cup-shaped body 168. A needle 170 may be secured to the plunger 162 and may extend through the first septum 116 and cannula 148 when the plunger 162 is in the retracted position.

In operation, the user-patient (or medical practitioner) may secure the base 106 to skin of the user-patient, for example, as previously described. Once the base 106 is secured to the skin of the user-patient, the user-patient (or medical practitioner) may activate the needle-inserting device 144 to cause the plunger 162 to move from the retracted position to the extended position E and, as a result of such movement, to cause the insert structure 166 to be moved into an opening into the interior of the housing 104. Upon movement of the insert structure 166 into the housing 104, the insert structure 166 may connect to the housing 104 by any suitable connection structure.

As discussed above, in particular embodiments, one or the other of the cup-shaped body 168 of the insert structure 166 and the housing 104 may include one or more flexible pawls, protrusions, indentations, or the like, for engaging and receiving one or more corresponding pawls, protrusions, indentations, or the like, on the other of the housing 104 and the insert structure 166 to provide a suitable connection structure. Alternatively or in addition, the connection structure may include adhesive material or other suitable connectors.

In particular embodiments, the housing 160 of the needle-inserting device 144 may automatically release from the base 106 upon movement of the plunger 162 and the insert structure 166 from the retracted position to the extended position E. For example, the housing 160 of the needle-inserting device 144 may be made of a material that has sufficient rigidity to operate as described herein, but also has a suitable flexibility (at least at the portion of the device 144 that connects to the housing 104) to bend away from and release from the housing 104 upon movement of the insert structure 166 to the extended position E.

In some embodiments, such as the embodiment shown in FIG. 16, a portion 172 of the internal surface of the housing 160 may include a ramped, wedge-shaped, or angled (relative to an axial direction of the housing 144, cannula 148, and needle 170) cross-sectional shape that engages an outer peripheral surface of the insert structure 166 and/or the plunger 162 as the insert structure 166 and plunger 162 are moved toward the extended position E. By engaging the angled, ramped, or wedge-shaped portion 172 of the internal surface of the housing 160, the plunger 162 and/or the insert structure 166 may cause the wall(s) of the housing 160 to flex outward as the plunger 162 and/or insert structure 166 are moved into the extended position. One or more slots, grooves, or the like 174 may be formed in the housing 166 to enhance the ability of the wall(s) of the housing 160 to flex outward. One or more protrusions 176 and/or indentations may be provided on one or the other of the interior surface of the housing 166 and the exterior surface of the housing 104 for engaging one or more corresponding indentations 178 and/or protrusions in the other of the housing 104 and housing 166 when the plunger 162 and insert structure 166 are in the retracted state shown in FIG. 16.

The one or more protrusions 176 and the one or more indentations 178, when engaged, may lock the housing 160 of the needle-inserting device 144 to the housing 104. The one or more protrusions 176 and/or indentations 178 may disengage from each other when the wall(s) of the housing 160 are flexed outward by the movement of the plunger 162 and the insert structure 166 to the extended position E. As a result, the housing 160 of the needle-inserting device 144 may be automatically disengaged and released from the housing 104 upon movement of the plunger 162 and insert structure 166 to the extended position E.

After movement of the plunger 162 and insert structure 166 from the retracted position (shown in FIG. 16) to the extended position E at which the insert structure 166 may be locked into the housing 104, while the housing 160 of the needle-inserting device 144 is released from the housing 104, the bias member 164 (or a second bias member (not shown)) may act on the needle 170 to move the needle 170 toward the retracted position and, thus, withdraw the needle 170 from the cannula 148. For example, a return motion of the coil spring after moving from the retracted position to the extended position E may provide sufficient force to withdraw the needle 170 from the cannula 148.

Once the insert structure 166 has been locked into place within the housing 104 and the needle-inserting device 144 has been removed from the housing 104, the cannula 148 may be connected in fluid-flow communication with a connection portion 130 of a second member such as, but not limited to, a reservoir, in a manner similar to the manner in which the first member 102 and the second member 103 are connectable in the embodiments of FIGS. 7-12. More specifically, the housing 104 may form a receptacle (similar to the receptacle 110 described above for FIGS. 7-12) and may contain the first septum 116.

Similar to the embodiment of FIGS. 7-12, the connection portion 130 may also include a second septum 136. In particular, the connection portion 130 may be inserted into the receptacle formed by the housing 104 to connect the interior of the reservoir in fluid-flow communication with the cannula 148. The cannula 148 in FIG. 13 may include a sharp end 148*a* adjacent the first septum 116. As the connection portion 130 is inserted into the housing 104, the connection portion may push the first septum 116 against the sharp end 148*a* of the cannula 148 to cause the sharp end 148*a* of the cannula 148 to pierce the first septum 116. Further insertion motion of the connection portion 130 into the housing 104 may cause the sharp end 148*a* of the cannula 148 to pierce the second septum 136 in the connection portion 130 to form a flow path from or to the connection portion 130 through the cannula 148.

FIGS. 17-20 illustrate an inserting system 200 according to an embodiment of the present invention. Although the inserting system 200 may be similar or used with the embodiments of FIGS. 1-16, it should be understood that the inserting system 200 may also include some or all of the same components and operate in a manner similar to that shown and described in the embodiments of FIGS. 22-26. In addition, some or all of the features shown in FIGS. 1-16 and 22-26 may be combined in various ways and included in the embodiment shown in FIGS. 17-20.

The inserting system 200 may include a first member 202, which may be similar to the first member 102 (e.g., FIGS. 7-12). The first member 202 may include a housing 204 on a base 206. The housing 204 may be formed integral with the base 206 or may be formed as a separate structure connected to the base 206 in a fixed relation to the base 206. The housing 204 and the base 206 each may be made of any suitably rigid material, including, but not limited to plastic, metal, ceramic, composite material, or the like.

The housing 204 may include an injection site section 205 containing an injection site structure in which a hollow needle or cannula may be inserted into a user-patient for conveying fluidic media to or from the user-patient. In other embodiments, instead of or in addition to an injection site, the housing 204 may contain, be part of, or be operatively connected to any other suitable structure for conveying, containing, and/or processing fluidic media.

The first member 202 may be operatively connectable to a second member (not shown), which may be similar to the second member 103 (e.g., FIGS. 7-12). As previously described with respect to FIGS. 7-12, the second member may also include a housing 108, which in the illustrated embodiment may include a reservoir 107 for containing fluidic media. The second member may be held within or otherwise be covered by an outer housing 109 configured to attach to the base 106. The outer housing 109 may be configured to connect to the base 206 (FIGS. 17-20) of the first member 202 (FIGS. 17-20) by any suitable connection structure. In some embodiments, upon coupling the first member 202 and the second member, fluid flow communication may be provided between the second member and the injection site section 205 in the first member 202.

In particular embodiments, at least one of the outer housing 109 and the base 206 (FIGS. 17-20) may include one or more flexible pawls, protrusions, indentations, or the like for engaging and/or receiving one or more corresponding pawls, protrusions, indentations, or the like on the other of the base 206 (FIGS. 17-20) and the outer housing 109 to provide a suitable connection structure. Alternatively or in addition, the connection structure may include adhesive material or other suitable connectors.

Returning to FIGS. 17-20, the housing 204 may have or be connected to a receptacle structure 210 having a chamber 214. The receptacle structure 210 may be similar to the receptacle structure 110 (e.g., FIGS. 7-12) previously described. In some embodiments, the receptacle structure 210 may be part of the housing 204 adjacent a section of the housing 204 containing the injection site section 205. In other embodiments, the receptacle structure 210 may include a further housing connected to the housing 204.

A fluid conduit 224, such as, but not limited to, a needle or the like may be supported within the chamber 214. The fluid conduit may be supported by a supporting structure located within the receptacle structure 210. In some embodiments, the supporting structure may be a wall integral with the receptacle structure 210. In other embodiments, the supporting structure may be any suitable structure that is generally fixed relative to the receptacle structure 210 and is able to support the fluid conduit 224 in a generally fixed relation to the receptacle structure 210.

The fluid conduit 224 may be made of any suitably rigid material, including, but not limited to metal, plastic, ceramic, or the like, and may have a hollow channel extending in a lengthwise dimension of the fluid conduit 224. The hollow channel in the fluid conduit 224 may be open at a location (not shown) along the lengthwise dimension of the fluid conduit 224, such as, but not limited to, a first end of the fluid conduit 224. The hollow channel in the fluid conduit 224 may be open at another location 224b along the lengthwise dimension of the fluid conduit 224, such as, but not limited to, a second end of the fluid conduit 224 opposite the first end of the fluid conduit 224. One of the openings in the fluid conduit 224 may be provided with a septum 226 that may be pierceable by a needle (not shown), for example as previously described, when a reservoir is connected to the first member 202

The injection site section 205 may include a channel 240 extending through the housing 204 and the base 206. The channel 240 may have an open end 240a on a bottom surface (relative to the orientation shown in FIG. 18) of the base 206. The channel 240 may have another open end 240b at an upper surface (relative to the orientation shown in FIG. 18) of the injection site section 205 of the housing 204. The channel 240 may include a channel section 242 having a larger radial dimension relative to a remaining portion of the channel 240 and may have a suitable shape and size to receive an insert structure, a needle, and/or a cannula, as will be described.

The system 200 may include an insertion housing 280. The insertion housing 280 may be made of a material of suitable strength and durability such as, but not limited to, plastic, metal, glass, or the like. The insertion housing 280 may be located adjacent the open end 240b of the channel 240 and arranged to selectively extend a needle and/or cannula of an insert structure into the open end 240b of the channel 240 and at least partially through the channel 240 as will be described.

The insertion housing 280 may be a separate device from the housing 204 and may be selectively engaged or connected to, for example in alignment with the channel 240, and disengaged or disconnected from the injection site section 205 and/or the first member 202 or portion thereof. In some embodiments, the insertion housing 280 may be recommended for disposal after a specified number of uses.

Figure 18:
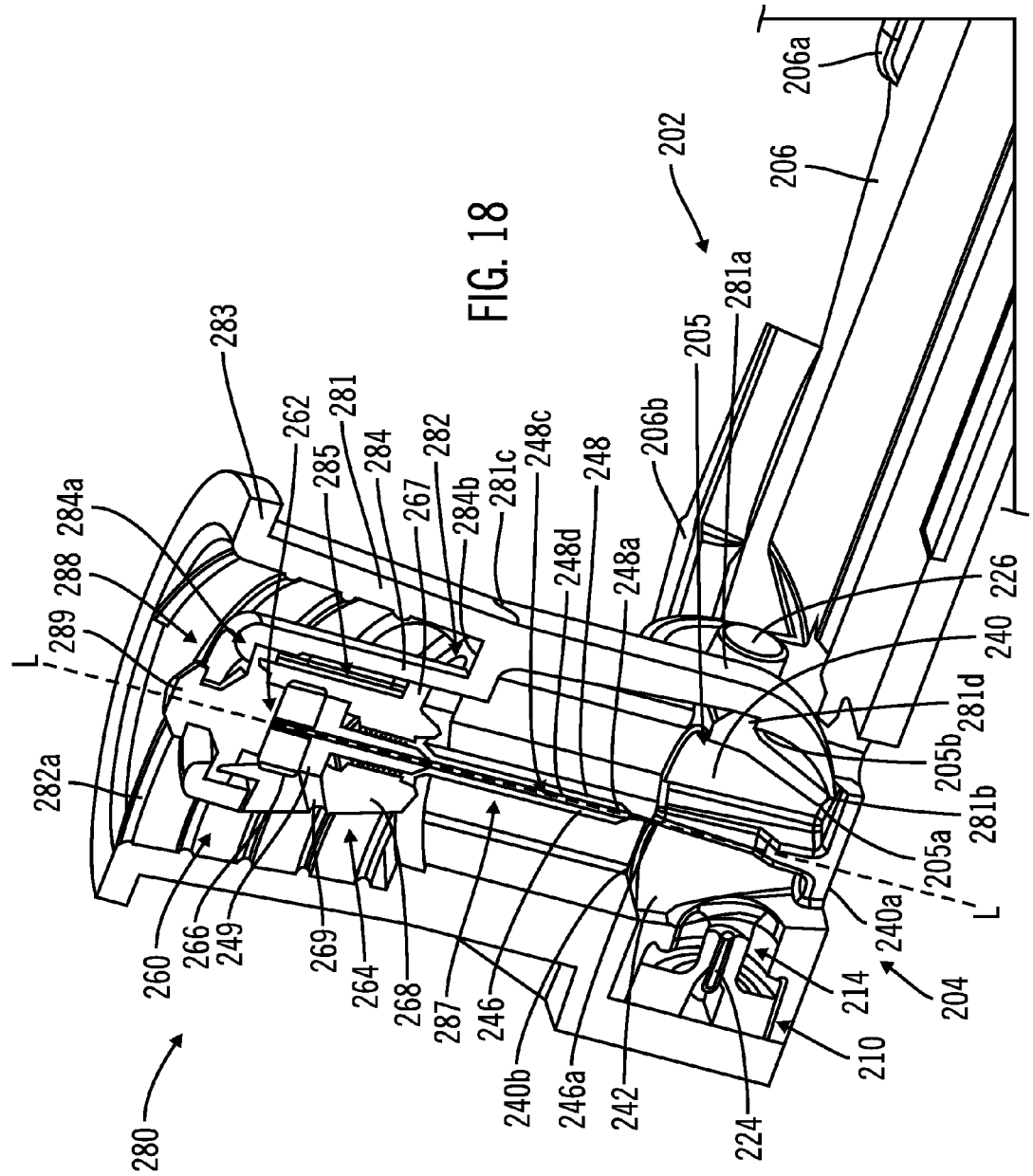
FIG. 18 illustrates a medial device in accordance with an embodiment of the present invention.
Figure 19:
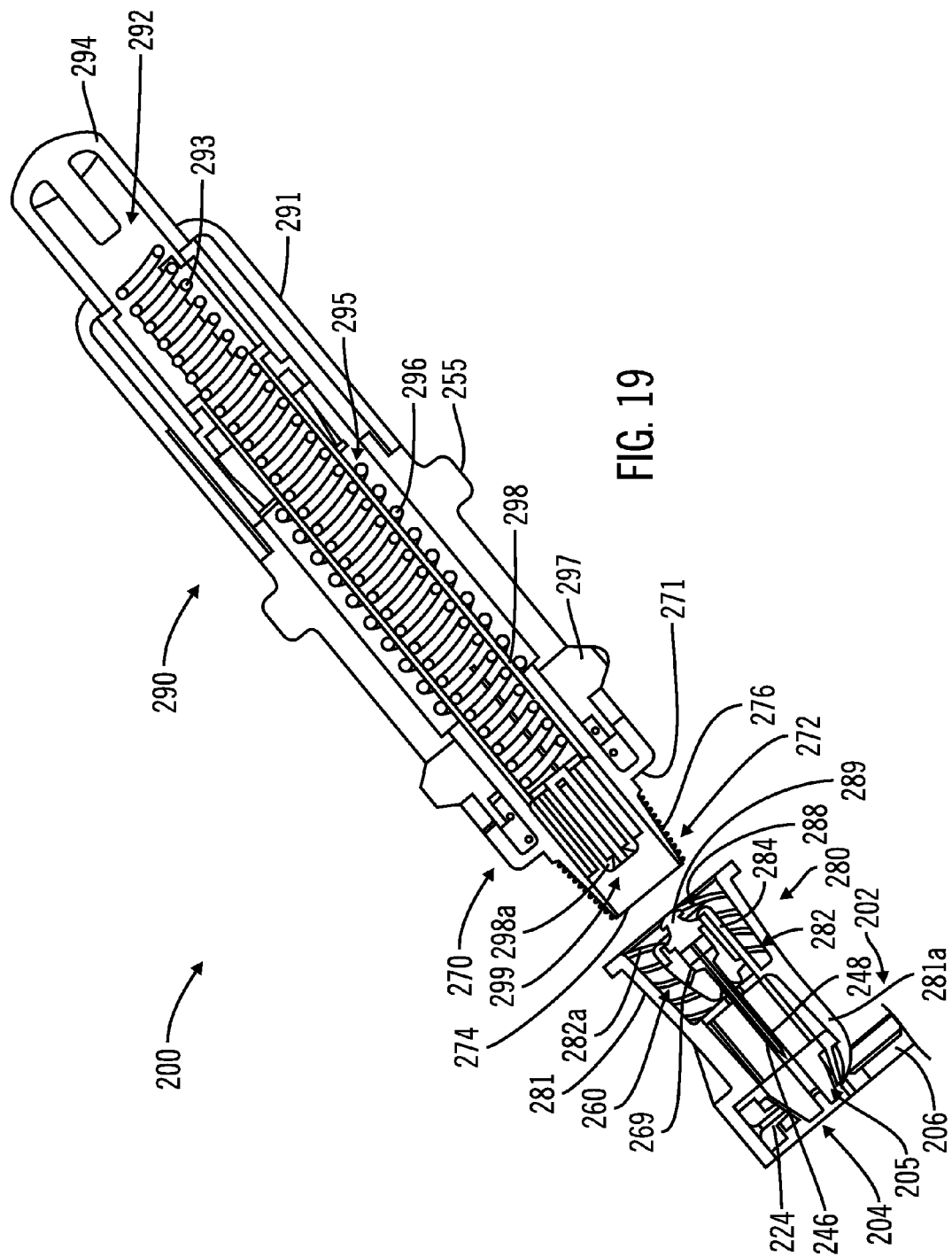
FIG. 19 illustrates a medial device in accordance with an embodiment of the present invention.
Figure 20:
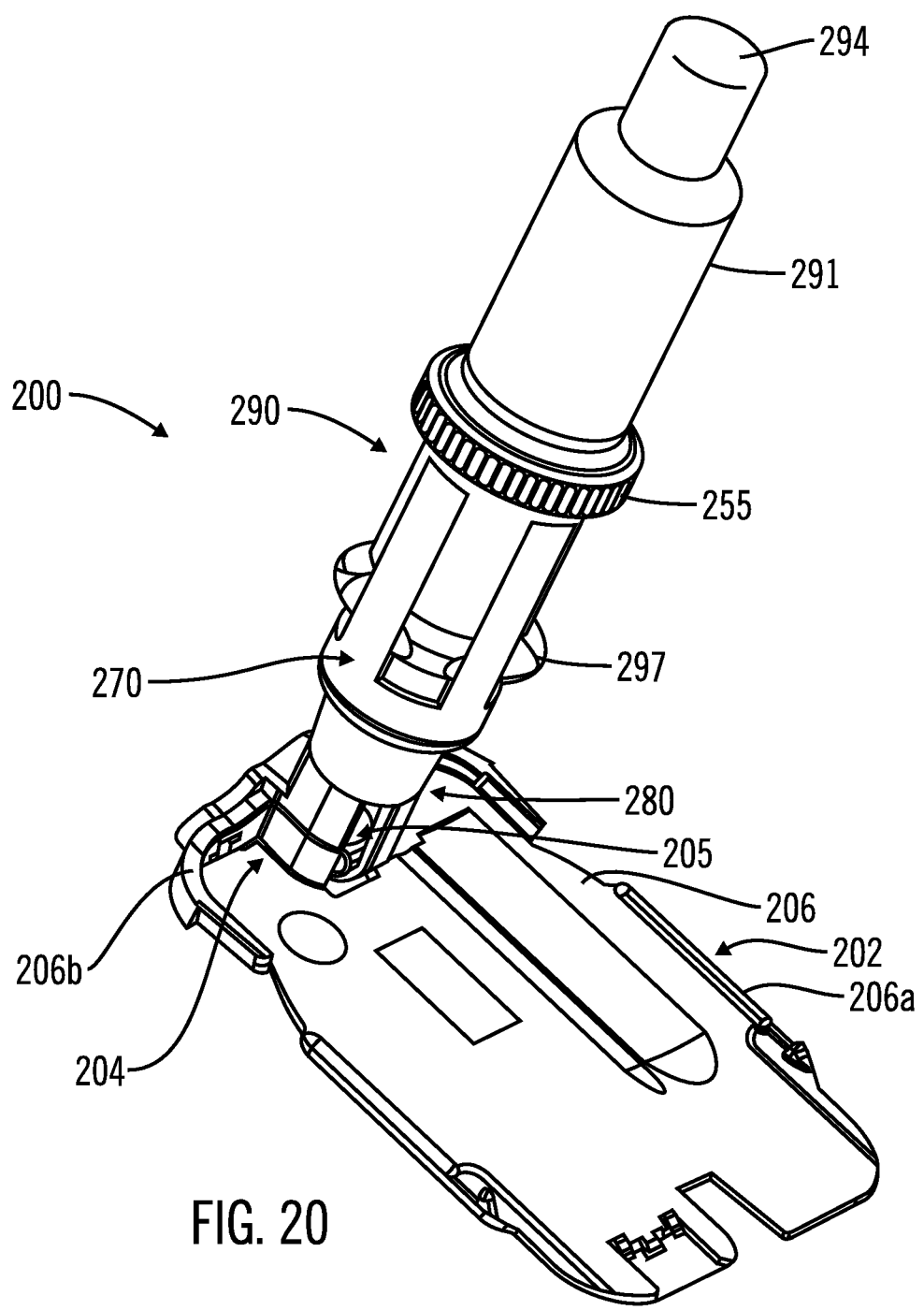
FIG. 20 illustrates a medial device in accordance with an embodiment of the present invention.

In the drawing of FIG. 18, the insertion housing 280 is shown as connected to the injection site section 205. With reference to FIGS. 17-20, a suitable connection structure may be provided on the insertion housing 280, the injection site section 205, and/or the first member 202 or portion(s) thereof to provide a manually releasable connection between those components. For example, the connection structure may include, but is not limited to, a threaded extension on one or the other of the insertion housing 280 and the injection site section 205 and a corresponding threaded receptacle on the other of the injection site section 205 and the insertion housing 280 for receiving the threaded extension in threaded engagement. In other embodiments, other suitable connection structures may be employed. These may include, but are not limited to, friction-fitted sections, flexible pawls or extensions on one or the other of the insertion housing 280 and the injection site section 205 (or the first member 202 or portion thereof) and a corresponding aperture, stop surface, or the like on the other of the injection site section 205 (or the first member 202 or portion thereof) and the insertion housing 280.

In some embodiments, the insertion housing 280 may include one or more arm 281*a* having an end 281*b* and/or a locking surface 281*d* adapted to operatively engage with and disengage from the first member 202, such as an aperture 205*a* and/or a retaining surface 205*b*, respectively, of the insertion site section 205, or the like. In some embodiments, the arm 281*a* may be integral with the insertion housing 280 and the arm 281*a* may be sufficiently flexible to operatively engage with and disengage from an engagement portion of the first member 202 as the arm 281*a* flexes toward and away from the first member 202. In other embodiments, the arm 281*a* may be operatively connected with the insertion housing 280. For example, the arm 281*a* may be adapted to pivot about a point 281*c* to allow the arm 281*a* to operatively engage with and disengage from the first member 202 as the arm 281 pivots toward and away from the engagement portion of the first member 202. The engagement portion may be, but is not limited to, an aperture, a ridge, an undersurface (or upper surface), a protrusion, a tab, an arm, a bias member, or any other suitable structure or mechanism arrangeable to allow the arm 281 to engage and/or disengage.

The insertion housing 280 may contain a main chamber 287 in alignment with the opening 240*b*. The insertion housing 280 may have a longitudinal dimension and a moveable insert structure 260 located within the insertion housing 280 and moveable along the longitudinal dimension in a direction L. The insert structure 260 may be moveable at least between a first position and a second position. The insert structure 260 may include a first part 262 and a second part 264 operatively connected to the first part 262 so that the first part 262 and the second part 262 may move together along the longitudinal dimension of the insertion housing 280. The insert structure 260 may be biased toward or otherwise held in the first position until sufficient force is applied to the insert structure 260 to move or otherwise actuate the insert structure 260 to the second position.

Various examples of suitable structures for insert structures are described in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various insert structures are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method,", all of which are herein incorporated by reference in its entirety. Other examples of suitable structures for insert structures are described herein.

The first part 262 of the insert structure 260 may include a plunger head 288 and a needle 246 supported by the plunger head 288. The second part 264 of the insert structure 260 may include a collar 268 and a cannula 248 supported by the collar 268. The plunger head 288 may be connected to the collar 268. The first part 262 and the second part 264 may be configured to be removably attachable from each other, for example, in a friction fit engagement, snap fit engagement, or the like. For example, one of the plunger head 288 and the collar 268 may include protrusions or the like and the other of the plunger head 288 and the collar 268 may include apertures for receiving the protrusions.

The cannula 248 may extend at least partially through the collar 268. The cannula 248 may be fixed to the collar 268 to move with movement of the insert structure 260. The cannula 248 may have a hollow central channel 248*c* extending along a longitudinal length of the cannula 248 and open at one end 248*a* that may be adjacent a sharp end 246*a* of the needle 246 disposed within the cannula 248 as will be discussed. An end 248*b* of the cannula 248 opposite the open end 248*a* may have a head 249 having a larger radial dimension than a shaft portion 248*d* of the cannula 248.

A septum 266 may be supported or otherwise retained by the collar 268. The septum 266 may be a resealable member made of silicone, plastic, rubber, or the like. The septum 266 may be arranged between the plunger head 288 and the collar 268. The septum 266 may be pierceable by the needle 246.

The needle 246 may be arranged to extend through at least a portion of the cannula 248. The needle 246 may be supported by, secured, or operatively connected to the plunger head 288 to move with movement of the insert structure 260. Thus, in some embodiments, the plunger head 288 and the needle 246, which may be both part of the first part 262 of the insert structure 260, and the collar 268 and the cannula 248, which may be both part of the second part 264 of the insert structure 260, may be moveable at least between a first position and a second position.

In the second position, the needle 246 and the cannula 248 may extend through the opening 240*b* of the channel 240 and at least partially through the channel 240. As such, the sharp end 246*a* of the needle 246 and at least a portion of the length of the cannula 248 may extend out the opening 240*a* of the channel 240, for example, into skin of a user-patient.

The collar 268 of the insert structure 260 may have a suitable shape and size to fit into the channel section 242 of the channel 240 when the insert structure 260 is moved to the second position, for example, by an actuation device as will be discussed later. In particular embodiments, the collar 268 may include one or more protrusions 267 and/or indentations that engage with one or more corresponding indentations, such as the aperture 205*a*, and/or protrusions in the injection site section 205 to provide a friction fit, snap fit, or the like, to lock or retain the second part 264 within the injection site section 205 upon the insert structure 260 being moved to the second position.

In further embodiments, instead of or in addition to engaging protrusions and indentations, one or more other mechanical structures may be employed to provide a suitable retaining function for retaining the second part 264 in place within the injection site section 205 upon the insert structure 260 being moved to the second position, for example, by an actuation device, including, but not limited to, a friction fit structure, snap fit structure, or the like.

In various embodiments, the arm 281*a* of the insertion housing 280 may be actuated to disengage the insertion housing 280 automatically from the first member 202 upon the insert structure 260 being moved to the second position. For example, the arm 281*a* may be adapted to flex or pivot away from the insertion housing 280 to disengage the first member 202 when the insert structure 260 is moved to the second position. In moving to the second position, one of the protrusions 267 may push against the end 281b of the plunger arm 281a located in the aperture 205a. This may displace the end 281b of the plunger arm 281 and release the plunger arm 281a and/or the locking surface 281d from the retaining surface 205b from the first member 202. Accordingly, in such embodiments, the insertion housing 280 may be removed. In some embodiments, removal of the insertion housing 280 also removes the first part 262 that may include the needle 246 and the plunger 288, while leaving the second part that may include the cannula 248 and the collar 268 engaged to the injection site section 205.

The collar 268 may have a connection channel 269 provided in fluid flow communication with an opening (not shown) in the cannula 248 in fluid flow communication with the hollow central channel 248c of the cannula 248. Accordingly, the connection channel 269 may be in fluid flow communication with the hollow central channel 248c of the cannula 248. The connection channel 269 may be provided along the collar 268 at a location at which the connection channel 269 may align with the fluid conduit 224 when the insert structure 260 has been moved to the second position. Thus in some embodiments, in a case where the first member 202 and the second member are brought together (e.g., FIG. 9) and the insert structure 260 is in the second position, a fluid flow path may be established between the reservoir in the second member and the cannula 248 via the fluid conduit 224 and the connection channel 269.

In some embodiments, the insertion housing 280 may include an inner housing portion 284 concentrically arranged within an outer housing portion 281. The inner housing portion 284 may have an inner chamber 285 in alignment with the chamber 287 in which the insert structure 260 may be arranged for movement. A lip portion 284a or the like extending from the inner housing portion 284 may be for containing the insert structure 260 in the inner chamber 285. For example, the insert structure 260 may be in contact with the lip portion 284a when the insert structure 260 is in the first position. The outer housing 281 may have an outer chamber 282 between the outer housing 281 and the inner housing portion 284. The outer chamber 282 may be for receiving at least a portion of an actuation device for actuating the plunger head 288 as will be described. In various embodiments, the inner housing portion 284 may be integral with or made separate and connected with the outer housing portion 281.

As previously discussed, in various embodiments, the insert structure 260 (i.e., the plunger head 288, the needle 246, the collar 268, and the cannula 248) may be actuated to move to the second position by an actuation device 290. The actuation device 290 may include a housing 291 securable to the insertion housing 280. A suitable connection structure may be provided on the actuation device 290 and/or the insertion housing 280 to provide a manually releasable connection between those components. In some embodiments, the connection structure may include, but is not limited to, a threaded extension on one or the other of the actuation device 290 and the insertion housing 280 and a corresponding threaded receptacle on the other of the insertion housing 280 and the actuation device 290 for receiving the threaded extension in threaded engagement.

For example, an end 272 of a distal portion 270 of the actuation device 290 may be adapted to be insertable into the insertion housing 280, for example, within the outer chamber 282. The distal portion 270 may have a threaded portion 276 for threaded engagement of a threaded portion 282a within the insertion housing 280. The end 272 may be insertable into the outer chamber 282 of the insertion housing 280, for example, until a surface 271 of the actuation device 290 abuts a lip portion 283 of the insertion housing 280 and/or the end 272 contacts a floor 284b of the insertion housing 280.

In other embodiments, other suitable connection structures may be employed. Such a connection structure may include, but is not limited to, friction-fitted sections of the insertion housing 280 and the actuation device 290, flexible pawls or extensions on one or the other of the actuation device 290 and the insertion housing 280 and a corresponding aperture, stop surface, or the like on the other of the insertion housing 280 and the actuation device 290.

The housing 291 may contain an internal chamber 292 having a longitudinal dimension and a member 298 arranged within the housing 291. The member 298 may be moveable in the direction L at least between a first position (e.g., FIG. 19) and a second position. The housing 291 may include a drive mechanism for actuating the member 298. The drive mechanism may be a bias member 293, such as, but not limited to, a coil spring, or the like, arranged within the internal chamber 292 of the housing 291. The bias member 293 may be configured to impart a bias force on the member 298 when the member 298 is in the first position to urge the member 298 toward the second position.

In some embodiments, an activation structure, such as a trigger, button, or the like, may be provided to control the actuation device 290. In further embodiments, a first trigger 294 may be configured to arm or prepare the actuation device 290 for firing or otherwise moving the member 298 to move the insert structure 260. For example, the first trigger 294 may be pressed to retract the member 298 to the first position. As such, the first trigger 294 may be adapted to selectively arm the member 298 and/or the bias member 293 into the first position (i.e., the retracted position).

A second trigger 297 or the like may be configured to selectively release the member 298 and/or the bias member 293 to allow the member 298 to move in the direction L under the force of the bias member 293 to the second position. In other embodiments, the first trigger 294 may be configured to selectively release the member 298 and/or the bias member 293 to allow the member 298 to move in the direction L under the force of the bias member 293 to the second position upon being operated after the actuation device 290 has been armed. For example, pressing the first trigger 294 a first time may retract the member 298 to the first position, and pressing the first trigger 294 a second time may release or otherwise allow the member 298 to advance to the second position. Other examples of insertion structures are described in U.S. Pat. Pub. No. US 2007/0142776, entitled "Insertion Device for an Insertion Set and Method of Using the Same," which is herein incorporated by reference in its entirety.

In yet further embodiments, a first locking mechanism (not shown) may be provided such as, but not limited to, a manually moveable projection, lever, slider, or the like. The first locking mechanism may be connected to or extending through the housing 291 and engaging the member 298 (or other structure holding the member 298) in a releasable manner to selectively hold the member 298 in the retracted position, for example after the first trigger 294 has been operated, against the bias force of the bias member 293.

In some embodiments, the actuation device 290 may be configured to allow the member 298 to be moved from the second position at least toward the first position automatically or upon manipulation by the user, for example, to a third position or a neutral position (e.g., position of the member before being moved to the first position when the actuation device is armed). That is, after the member 298 has been moved to the second position (e.g., an extended position), the member 298 may be moved to a third position automatically or upon manipulation of the actuation device 290 by the user-patient. The third position may be any suitable position at which the needle 246 is sufficiently withdrawn, for example, from the skin of the patient, as will be discussed, such as, but not limited to, the first position, a position between the first and second positions, or the like.

For example in some embodiments, the housing 291 may include a second chamber 295. The second chamber 295 may be concentrically arranged relative to the internal chamber 292, for example around the internal chamber 292. A drive mechanism may be arranged within the second chamber 295 of the housing 291 to move the member 298. The drive mechanism may be a second bias member 296, such as, but not limited to, a coil spring, or the like, arranged to impart a bias force on the member 298 when the member 298 is in the second position to urge the member 298 toward third position. Thus, in some embodiments, the member 298 can be moved to the first position (e.g., by pressing the first trigger 294), moved to the second position (e.g., by pressing the second trigger 297), and then automatically moved to a third position.

In some embodiments, an activation structure, such as a trigger (e.g., first trigger 294, second trigger 297, or a third trigger (not shown)), button or the like, may be provided to control movement of the member from the second position to the third position. Thus, in some embodiments, the member 298 can be moved to the first position (e.g., by pressing the first trigger 294), moved to the second position (e.g., by pressing the second trigger 297), and then further moved to a third position (e.g., by pressing the first trigger 294, the second trigger 297, or the like).

In yet further embodiments, a second locking mechanism (not shown) may be provided such as, but not limited to, a manually moveable projection, lever, slider, or the like. The second locking mechanism may be connected to or extending through the housing 291 and engaging the member 298 (or other structure holding the member 298) in a releasable manner to selectively hold the member 298 in the second position, for example after the second trigger 297 has been operated, against the bias force of the second bias member 296.

In various embodiments, the member 298 may be adapted to operatively engage the plunger head 288, for example, when the actuation device 290 is connected to the insertion housing 280. The member 298 or a portion thereof may be made of a sufficiently rigid material, but having a certain amount of flexibility. A protrusion, extension, arm, or the like may be provided on one or the other of the member 298 and the plunger 288 and a corresponding aperture, protrusion, extension, arm or the like on the other of the plunger 288 and the member 298 for engaging each other. For example, in particular embodiments, the member 298 may have one or more arms 299 for engaging a head portion 289 of the plunger head 288 upon the actuation device 290 being connected to the insertion housing 280.

Thus in some embodiments, in a case where the member 298 is operatively engaged with the plunger head 288 and the member 298 is actuated, the insert structure 260, which may include the plunger head 288, the needle 246, the collar 268, and the cannula 248, may be moved to the second position. Similarly as previously described, the member 298 can be further actuated to move the first part 262 of the insert structure 260, which may include the plunger head 288 and the needle 246, away from the first position (e.g., to (or toward) the first position and/or the third position). Thus, the second part of the insert structure 260, which may include the collar 268 and the cannula 248, may remain in the second position to allow fluid to flow from the reservoir though the fluid conduit 224 and the connection channel 269 to the cannula 248 into the user-patient as previously described.

In various embodiments, the actuation device 290 may be configured for improved handling of the actuation device 290 by the user-patient. For example, the actuation device 290 may include a handling portion 255, grips, textured surfaces, or the like that may aid in handling of the actuation device 290.

Figure 21:
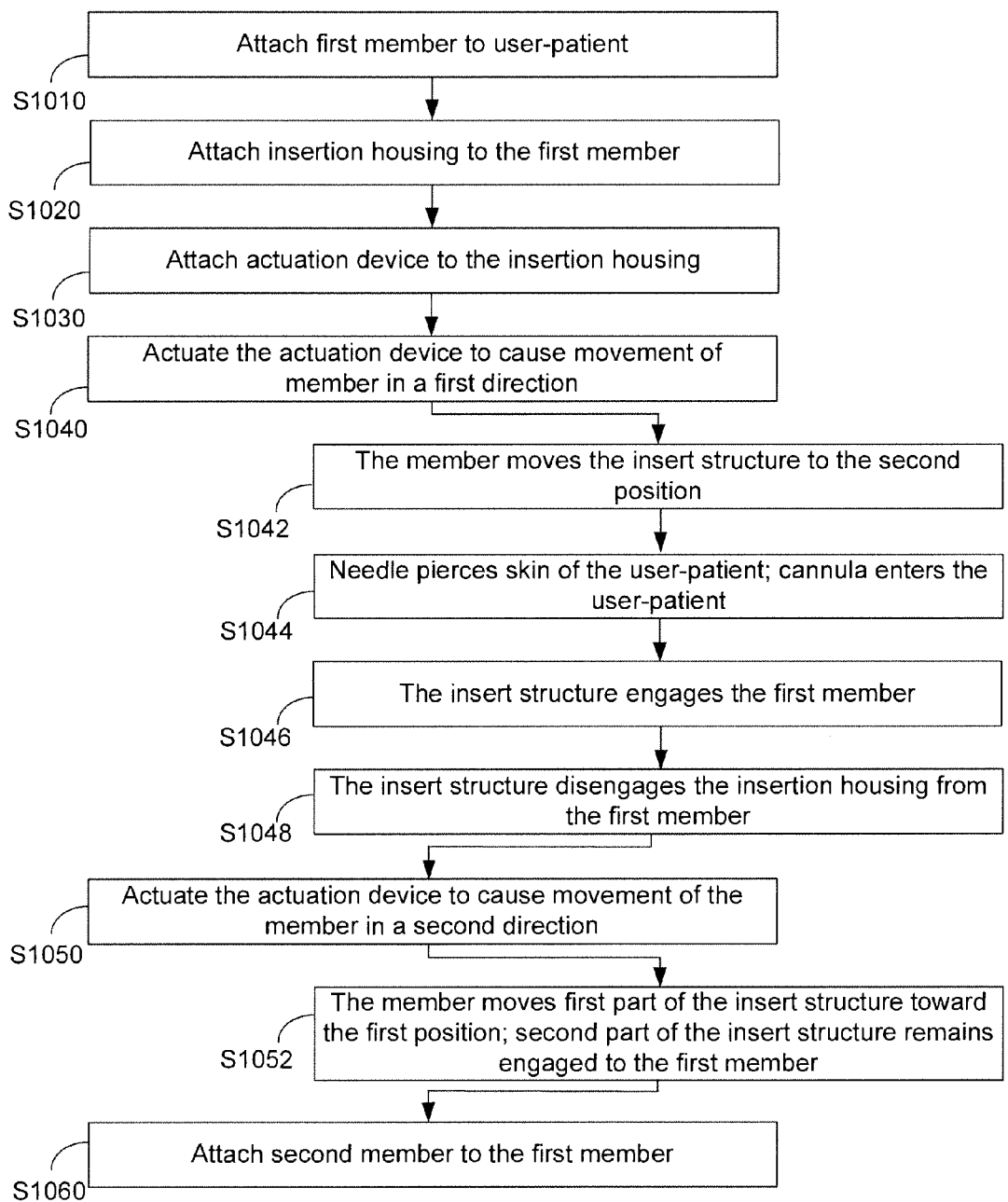
FIG. 21 illustrates flow chart for using a medial device in accordance with an embodiment of the present invention.

FIG. 21 illustrates a flowchart describing use of the system 200 (e.g., FIGS. 17-20) according to an embodiment of the present invention. With reference to FIGS. 17-21, the system 200 may be operated according to process 1000. In step S1010, the base 206 of the first member 202 may be secured to skin of a user-patient at a suitable injection location with, for example, but not limited to, adhesive material, or the like. Examples for securing the first member to the skin of the user-patient are described herein and can be found in U.S. patent application Ser. No. 11/645,435, filed Dec. 26, 2006, entitled "Infusion Medium Delivery system, Device And Method With Needle Inserter And Needle Inserter Device And Method" and U.S. patent application Ser. No. 12/027,963, filed Feb. 7, 2008, entitled "Adhesive Patch Systems and Methods," all of which are herein incorporated by reference in their entirety. Alternatively or in addition, the base 206 may be secured to the user-patient by one or more other suitable structures, including, but not limited to, straps, or the like.

Once the base 206 is suitably secured the user-patient at a suitable injection location, in step S1020, the insertion housing 280 may be affixed to the inject site section 205. Then, in step S1030, the actuation device 290 may be connected to the insertion housing 280 to operatively engage the member 298 with the plunger 288. Then in step S1040, the actuation device 290 may be actuated, for example by actuating one or more of the first trigger 294 and the second trigger 297, to move the member 298 to the second position.

In step S1042, the member 298 may move the insert structure 260, which may include the plunger 288, the needle 246, the collar 268, and the cannula 248, to the second position. As a result, in step S1044, the needle 246 may pierce the skin of the user-patient allowing a portion of the cannula 248 to enter the user-patient. In step S1046, the insert structure 260 may engage the inject site section 205 to retain the cannula 248 within the user-patient. The cannula 248 and collar 268 may be retained in the second position by engagement of, for example, the collar 268 and the injection site section 205, as previously described. As the insert structure 260 engages the inject site section 205, in step S1048, the insert structure 260 may cause the insertion housing 280 to disengage from the first member 202.

Next in step S1050, with the cannula 248 and the body 268 locked in the second position, the actuation device 290 may be further actuated, for example automatically or by operating one of the triggers, to cause movement of the member 298 to the third position. In step S1052, the member 298 may cause the first part 262 of the insert structure 260, which may include the plunger head 288 and the needle 246, to move away from the second part 264 of the insert structure 260 (e.g., toward the first position). The second part 262 of the insert structure 260 may remain in the inject site section 205 and the cannula 248 within the user-patient. In step S1060, the second member may be attached to the first member 202 to provide a fluid flow path from the reservoir of the second member to the user-patient via the fluid conduit 224, the connection channel 269 in the collar 268 of the insert structure 260, and the cannula 248. In other embodiments, such a flow path may be for conveying fluid from the user-patient to the reservoir.

A connection sequence (e.g., the sequence of connecting the actuation device 290 to the injection site section 205, connecting the first member 202 to the second member, attaching the base 206 of the first member 202 to the skin of the user-patient, etc.) for connecting various components may be different for different embodiments. For example, in some embodiments, the user-patient may be provided with a first member 202 having a base 206, a housing 204, and an injection site section 205 in a pre-connected state with the actuation device 290. In this manner, the user-patient need not have to connect the actuation device 290 to the housing 204 as those parts are supplied to the user in a pre-connected state, for example, from a manufacturing or assembly facility. In such embodiments, the base 206 of the first member 202 may be secured to skin of the user-patient at a suitable injection location. After securing the base 206 to the skin of the user-patient, the actuation device 290 may be activated to cause the insert structure 260 to move to the second position so that the needle 246 can pierce the skin of the user-patient.

While the connection sequence in some of the above embodiments involve securing the base 206 of the first member 202 to the user-patient prior to connection of the second member to the first member 202, in other embodiments, the second member may be connected to the first member 202, as described above, prior to securing the base 206 of the first member 202 onto the skin of the user-patient. In such embodiments, the first member 202 and the second member may be connected together and, thereafter, may be secured to the user-patient, for example, by adhering one or both of the first member 202 and the second member to the skin of the user-patient. In addition, while the connection sequence in the above embodiments involve activating the actuation device 290 prior to the connection of the second member to the first member 202, in other embodiments, the second member may be connected to the first member 202, as described above, prior to activating the actuation device 290.

In some embodiments, the receptacle 210 may be in the first member 202 and a connection portion may be in the second member. In other embodiments, the receptacle 210 may be in the second member, for example, in or associated with a housing for a reservoir, and the connection portion may be in the first member 202, for example, in or associated with a housing containing an injection site structure.

Figure 22:
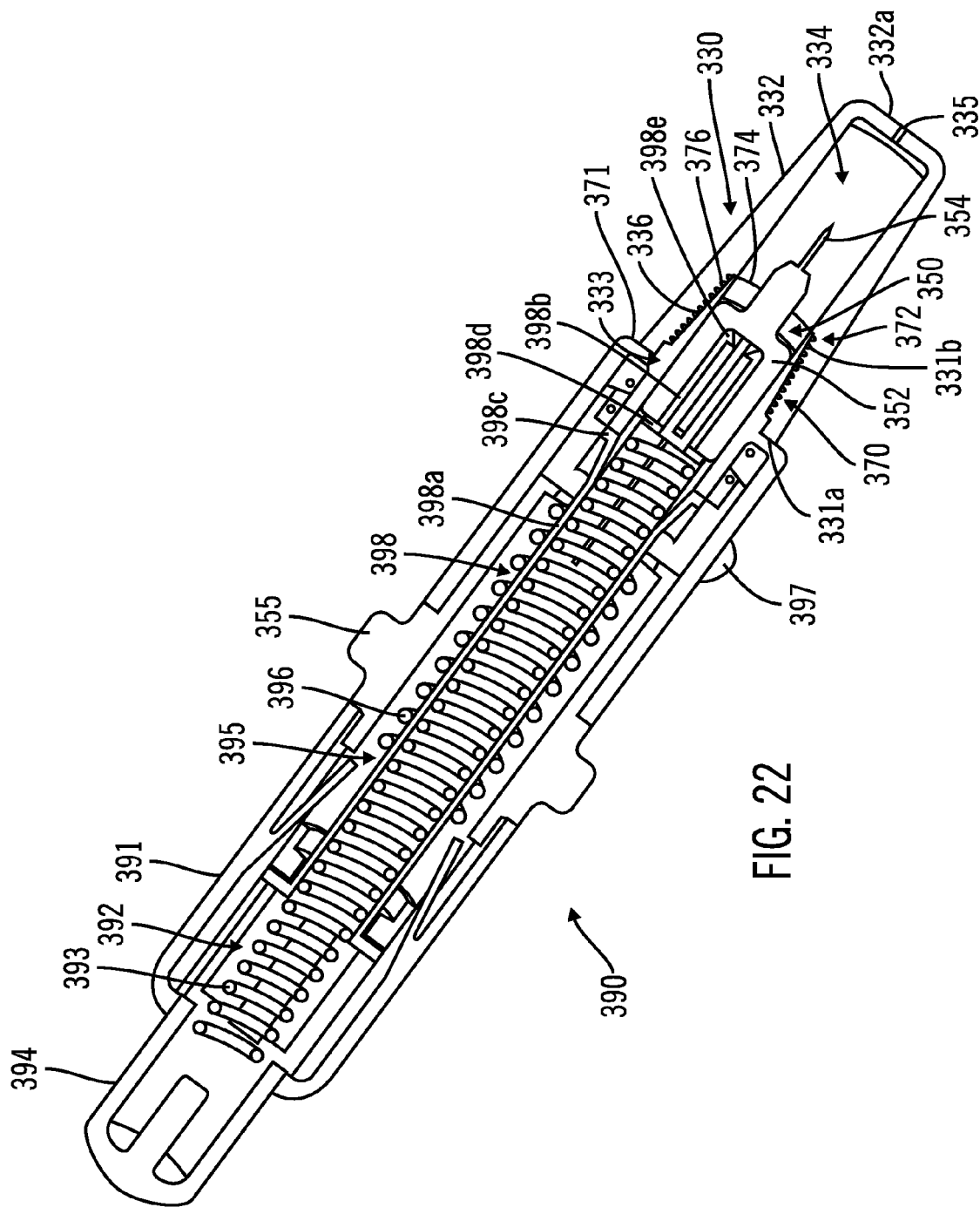
FIG. 22 illustrates a medial device in accordance with an embodiment of the present invention.
Figure 23:
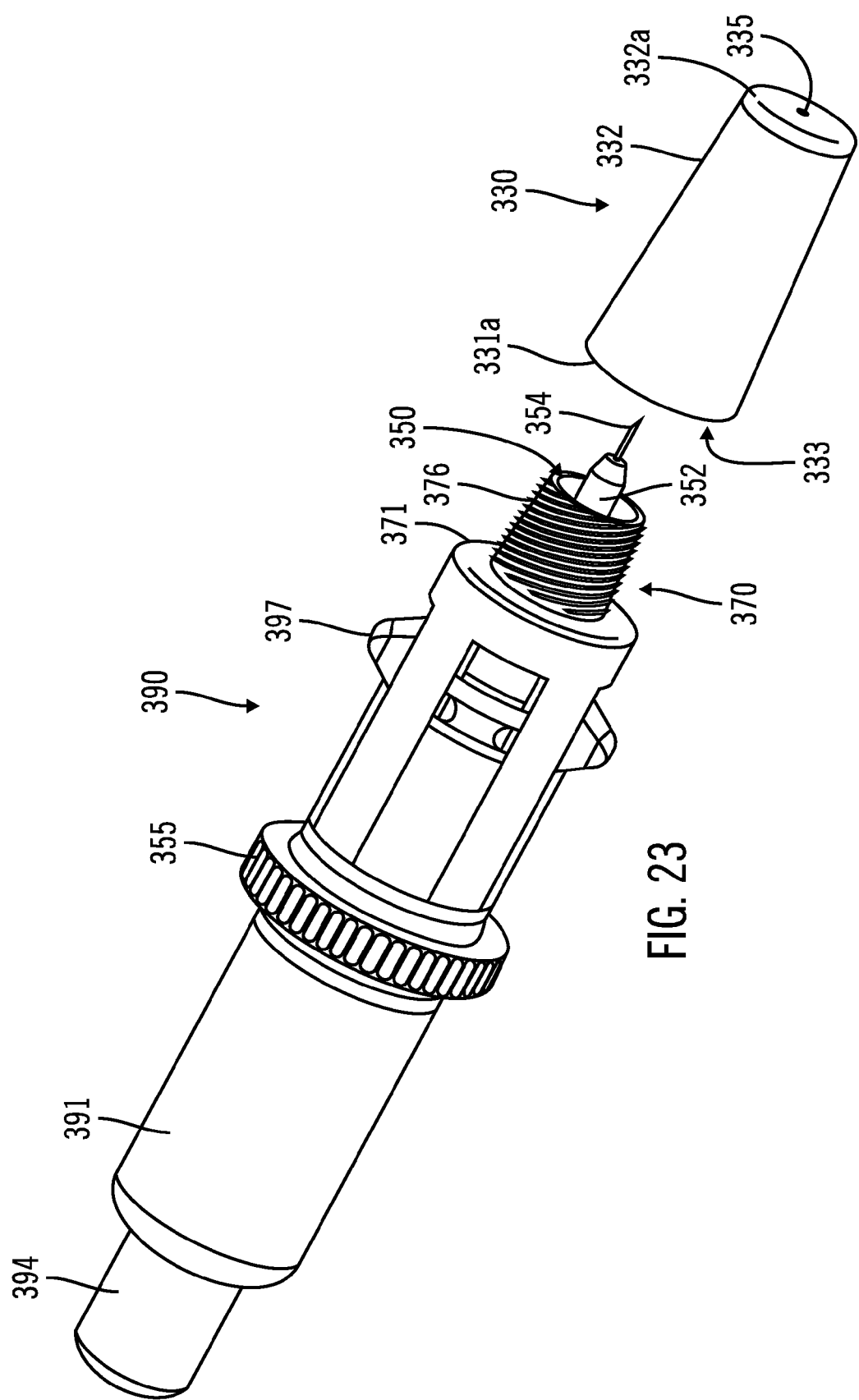
FIG. 23 illustrates a medial device in accordance with an embodiment of the present invention.

FIGS. 22 and 23 illustrate an actuation device 390 according to an embodiment of the present invention. Although the actuation device 390 may be similar or used with the embodiments of FIGS. 17-21, it should be understood that the actuation device 390 may also include some or all of the same components and operate in a manner similar to that shown and described in the embodiments of FIGS. 1-16 and 25-26. In addition, some or all of the features shown in FIGS. 1-21, 25, and 26 may be combined in various ways and included in the embodiment shown in FIGS. 22-23.

The actuation device 390 may be similar to the actuation device 290 (e.g., FIGS. 17-20). With reference to FIGS. 17-23, the actuation device 390 may include a housing 391 securable to the insertion housing 280. A suitable connection structure may be provided on the actuation device 390 and/or the insertion housing 280 to provide a manually releasable connection between those components. For example, the connection structure may be similar to the connection structure previously described for connecting the actuation device 290 to the insertion housing 280. In some embodiments, the connection structure may include, but is not limited to, a threaded extension on one or the other of the actuation device 390 and the insertion housing 280 and a corresponding threaded receptacle on the other of the insertion housing 280 and the actuation device 390 for receiving the threaded extension in threaded engagement.

For example, an end 372 of a distal portion 370 of the actuation device 390 may be adapted to be insertable into the insertion housing 280, for example, within the outer chamber 282. The distal portion 370 may have a threaded portion 376 for threaded engagement of a threaded portion 282a within the insertion housing 280. The end 372 may be insertable into the outer chamber 282 of the insertion housing 280, for example, until a surface 371 of the actuation device 390 abuts a lip portion 283 of the insertion housing 280 and/or the end 372 contacts a floor 284b of the insertion housing 280.

In other embodiments, other suitable connection structures may be employed. Such a connection structure may include, but is not limited to, flexible pawls or extensions on one or the other of the actuation device 390 and the insertion housing 280 and a corresponding aperture, stop surface, or the like on the other of the insertion housing 280 and the actuation device 390.

The housing 391 may contain an internal chamber 392 having a longitudinal dimension and a member 398 arranged within the housing 391. The member 398 may be moveable in the direction L at least between a first position and a second position. The housing 391 may include a drive mechanism for actuating the member 398. The drive mechanism may be a bias member 393, such as, but not limited to, a coil spring, or the like, arranged within the internal chamber 392 of the housing 391. The bias member 393 may be configured to impart a bias force on the member 398 when the member 398 is in the first position to urge the member 398 toward the second position.

In some embodiments, an activation structure, such as a trigger, button, or the like, may be provided to control the actuation device 390. In further embodiments, a first trigger 394 may be configured to arm or prepare the actuation device 390 for firing or otherwise moving the member 398 to move the insert structure 260. For example, the first trigger 394 may be manually pressed to retract the bias member 393 to the first position. As such, the first button 394 may be adapted to selectively arm the member 398 and/or the bias member 393 into the first position (i.e., the retracted position).

A second trigger 397 or the like may be configured to selectively release the member 398 and/or the bias member 393 to allow the member 398 to move in the direction L under the force of the bias member 393 to the second position. In other embodiments, the first trigger 394 may be configured to selectively release the member 398 and/or the bias member 393 to allow the member 398 to move in the direction L under the force of the bias member 393 to the second position upon being operated after the actuation device 390 has been armed. For example, pressing the first trigger 394 a first time may retract the member 398 to the first position, and pressing the first trigger 394 a second time may release or otherwise allow the member 398 to advance to the second position. Other examples of insertion structures are described in U.S. Pat. Pub. No. US 2007/0142776, entitled "Insertion Device for an Insertion Set and Method of Using the Same," which is herein incorporated by reference in its entirety.

In yet further embodiments, a first locking mechanism (not shown) may be provided such as, but not limited to, a manually moveable projection, lever, slider, or the like. The first locking mechanism may be connected to or extending through the housing 391 and engaging the member 398 (or other structure holding the member 398) in a releasable manner to selectively hold the member 398 in the retracted position, for example after the first trigger 394 has been operated, against the bias force of the bias member 393.

In some embodiments, the actuation device 390 may be configured to allow the member 398 to be moved from the second position at least toward the first position automatically or upon manipulation by the user, for example, to a third position or a neutral position (e.g., position of the member before being moved to the first position when the actuation device is armed). That is, after the member 398 has been moved to the second position (e.g., an extended position), the member 398 may be moved to a third position automatically or upon manipulation of the actuation device 390 by the user-patient. The third position may be any suitable position at which the needle 246 is sufficiently withdrawn, for example, from the skin of the patient, such as, but not limited to, the first position, a position between the first and second positions, or the like.

For example in some embodiments, the housing 391 may include a second chamber 395. The second chamber 395 may be concentrically arranged relative to the internal chamber 392, for example around the internal chamber 392. A drive mechanism may be arranged within the second chamber 395 of the housing 391 to move the member 398. The drive mechanism may be a second bias member 396, such as, but not limited to, a coil spring, or the like, arranged to impart a bias force on the member 398 when the member 398 is in the second position to urge the member 398 toward third position. Thus, in some embodiments, the member 398 can be moved to the first position (e.g., by pressing the first trigger 394), moved to the second position (e.g., by pressing the second trigger 397), and then automatically moved to a third position.

In some embodiments, an activation structure, such as a trigger (e.g., first trigger 394, second trigger 397, or a third or further trigger (not shown)), button or the like, may be provided to control movement of the member from the second position to the third position. Thus, in some embodiments, the member 398 can be moved to the first position (e.g., by pressing the first trigger 394), moved to the second position (e.g., by pressing the second trigger 397), and then further moved to a third position (e.g., by pressing the first trigger 394, the second trigger 397, or the like).

In yet further embodiments, a second locking mechanism (not shown) may be provided such as, but not limited to, a manually moveable projection, lever, slider, or the like. The second locking mechanism may be connected to or extending through the housing 391 and engaging the member 398 (or other structure holding the member 298) in a releasable manner to selectively hold the member 398 in the second position, for example after the second trigger 397 has been operated, against the bias force of the second bias member 396.

In various embodiments, the member 398 may be adapted to operatively engage the plunger head 288, for example, when the actuation device 390 is connected to the insertion housing 280. The member 398 or a portion thereof may be made of a sufficiently rigid material, but having a certain amount of flexibility. A protrusion, extension, arm, or the like may be provided on one or the other of the member 398 and the plunger 288 and a corresponding aperture, protrusion, extension, arm or the like on the other of the plunger 288 and the member 398 for engaging each other. For example, in particular embodiments, the member 398 may have one or more arms 399 for engaging a head portion 289 of the plunger head 288 upon the actuation device 390 being connected to the insertion housing 280.

Thus in some embodiments, in a case where the member 398 is operatively engaged with the plunger head 288 and the member 398 is actuated, the insert structure 260, which may include the plunger head 288, the needle 246, the collar 268, and the cannula 248, may be moved to the second position. Similarly as previously described, the member 398 can be further actuated to move the first part 262 of the insert structure 260, which may include the plunger head 288 and the needle 246, away from the first position (e.g., to (or toward) the first position and/or the third position). Thus, the second part of the insert structure 260, which may include the collar 268 and the cannula 248, may remain in the second position to allow fluid to flow from the reservoir though the fluid conduit 224 and the connection channel 269 to the cannula 248 into the user-patient as previously described.

In various embodiments, the actuation device 390 may be configured for improved handling of the actuation device 390 by the user-patient. For example, the actuation device 390 may include a handling portion 355, grips, textured surfaces, or the like that may aid in handling of the actuation device 390.

Additionally, the actuation device 390 may allow for lancing or piercing the skin of the user-patient, for example, to obtain a blood sample. A lancing portion 350 may be removably attachable to the actuation device 390. The lancing portion 350 may be attached to or within the distal portion 370 in a friction fit, snap fit, threaded engagement, or the like. The lancing portion 350 may be adapted to operatively engage the member 398 such that movement of the member 398 causes movement of the lancing portion 350.

In various embodiments, the lancing portion 350 may be adapted to be removably attachable from the actuation device 390. For instance, when the lancing portion 350 is not in use, for example, the actuation device 390 may be coupled with an insertion housing (e.g., 280 in FIGS. 17-20) for inserting a needle and a cannula into the skin of the user-patient as previously described. Moreover, when the actuation device 390 is not being used with the insertion housing, the lancing portion 350 may be attached to the actuation device 390 for piercing the skin of the user-patient. The lancing portion 350 may be made of a material of suitable strength and durability such as, but not limited to, plastic, metal, glass, or the like.

The lancing portion 350 may include a collar body 352 and a piercing member, such as a needle 354. The collar body 352 may be made of a material of suitable strength and durability such as, but not limited to, plastic, metal, glass, or the like. The needle 354 may be supported by the collar body 352 so that the needle 354 may move with the collar body 352. For example, the needle 354 may extend through the collar body 352 or be operatively connected to the collar body 352. As previously discussed, in a case where the lancing portion 350 is operatively engaged with the member 398 and the member 398 is actuated, the lancing portion 350 may be caused to move by the member 398. Accordingly, the needle 354 may be actuated to move and exit the actuation device 390 to "prick" or otherwise pierce the skin of the user-patient. In other embodiments, the piercing member (e.g., needle 354) may be connected to the member 398 such that movement of the member 398 causes movement of the piercing member.

In various embodiments, a penetration depth of the needle 354 into the skin of the user-patient may be adjustable. In some embodiments, the lancing portion 350 may be adapted to be arranged relative to the actuation device 390 to adjust the penetration depth of the needle 354. For example, by inserting the lancing portion 350 further into or further along the actuation device 390, the penetration depth of the needle 354 can be reduced accordingly. Conversely, the penetration depth of the needle 354 can be increased by arranging or otherwise extending the lancing portion 350 further from the actuation device 390. In some embodiments, the needle 354 may be adapted to be adjustable relative to the collar body 352 in a similar fashion to decrease or increase the penetration depth of the needle 354.

In some embodiments, the actuation device 390 may include an adjustment member (not shown) for selectively adjusting the penetration depth of the needle 354. The adjustment member may be an at least partially rotatable dial, a slide, a trigger, a button, or the like. The adjustment member may be operatively engaged with the member 398, the first bias member 393, the second bias member 396, the collar body 352 of the lancing portion 350, and/or the needle 354 so that the penetration depth of the needle 354 can be varied. For example, rotation of the adjustment member may cause the lancing portion 350, portion thereof, and/or operatively connected components to advance or retreat relative to the actuation device 390 to increase or decrease the penetration depth of the needle 354.

In some embodiments, the actuation device 390 may be adapted to engage with and disengage from a guard 330 or cover. The guard 330 may have a housing 332 having an interior chamber 334. The guard 330 may be made of a material of suitable strength and durability such as, but not limited to, plastic, metal, glass, or the like. A suitable connection structure, such as one of the connection structures previously described, may be provided on the actuation device 390 and/or the guard 330 to provide a manually releasable connection between those components. In some embodiments, the connection structure may include, but is not limited to, a threaded extension on one or the other of the actuation device 390 and the guard 330 and a corresponding threaded receptacle on the other of the guard 330 and the actuation device 390 for receiving the threaded extension in threaded engagement.

For example, the end 372 of the distal portion 370 of the actuation device 390 may be adapted to be insertable into the interior chamber 334 of the guard 330 through an opening 333 to attach the guard 330 to the actuation device 390. The distal portion 370 may have a threaded portion 376, which may or may not be similar to the threaded portion 276 for engaging the inserting housing 280, for threaded engagement of a threaded portion 336 within the guard 330. The end 372 may be insertable into the guard 330, for example, until a surface 371, which may or may not be similar to the surface 271, of the actuation device 390 contacts a portion, such as an outer surface 331a, of the guard 330 and/or the end 372 contacts a portion, such as an inner surface 331b, within guard 330. In other embodiments, a portion of the guard 330 may be configured to be insertable into the actuation device 390, for example through opening 374 through which the lancing portion 350 may be attached to the actuation device 390, to attach the guard 330 to the actuation device 390.

In other embodiments, other suitable connection structures may be employed for connecting the guard 330 with the actuation device 390. Such a connection structure may include, but is not limited to, flexible pawls or extensions on one or the other of the actuation device 390 and the guard 330 and a corresponding aperture, stop surface, or the like on the other of the other of the guard 330 and the actuation device 390.

An aperture 335 or the like may be provided on the housing 332 of the guard 330 and extending through to the interior chamber 334. The aperture 335 may be located on an end 332a opposite the opening 333. The aperture 335 may allow the needle 354 or a portion thereof to extend beyond the end 332a of the guard 330 to pierce the skin of the user-patient, for example, when the member 398 is actuated to move the lancing portion 350. In various embodiments, the guard 330 may be arrangeable to adjust the penetration depth of the needle 354. For example, by arranging the guard 330 (e.g., screwing on the guard 330) further into or further along the actuation device 390, the penetration depth of the needle 354 can be increased accordingly. Conversely, the penetration depth of the needle 354 can be decreased by arranging guard 330 further from the actuation device 390.

As previously discussed, in some embodiments, the actuation device 390 may be configured to retract the needle 354 automatically after the needle 354 pierces the skin of the user-patient. In such embodiments, the needle 354 may pierce or prick the skin of the user-patient and then return to a position (e.g., the third position) within the actuation device 390 and/or the guard 330. In other embodiments, the actuation device 390 may be configured such that the needle 354 can be manually retracted after piercing the skin of the user-patient, for example, by operating the second trigger 397, or the like.

Figure 24:
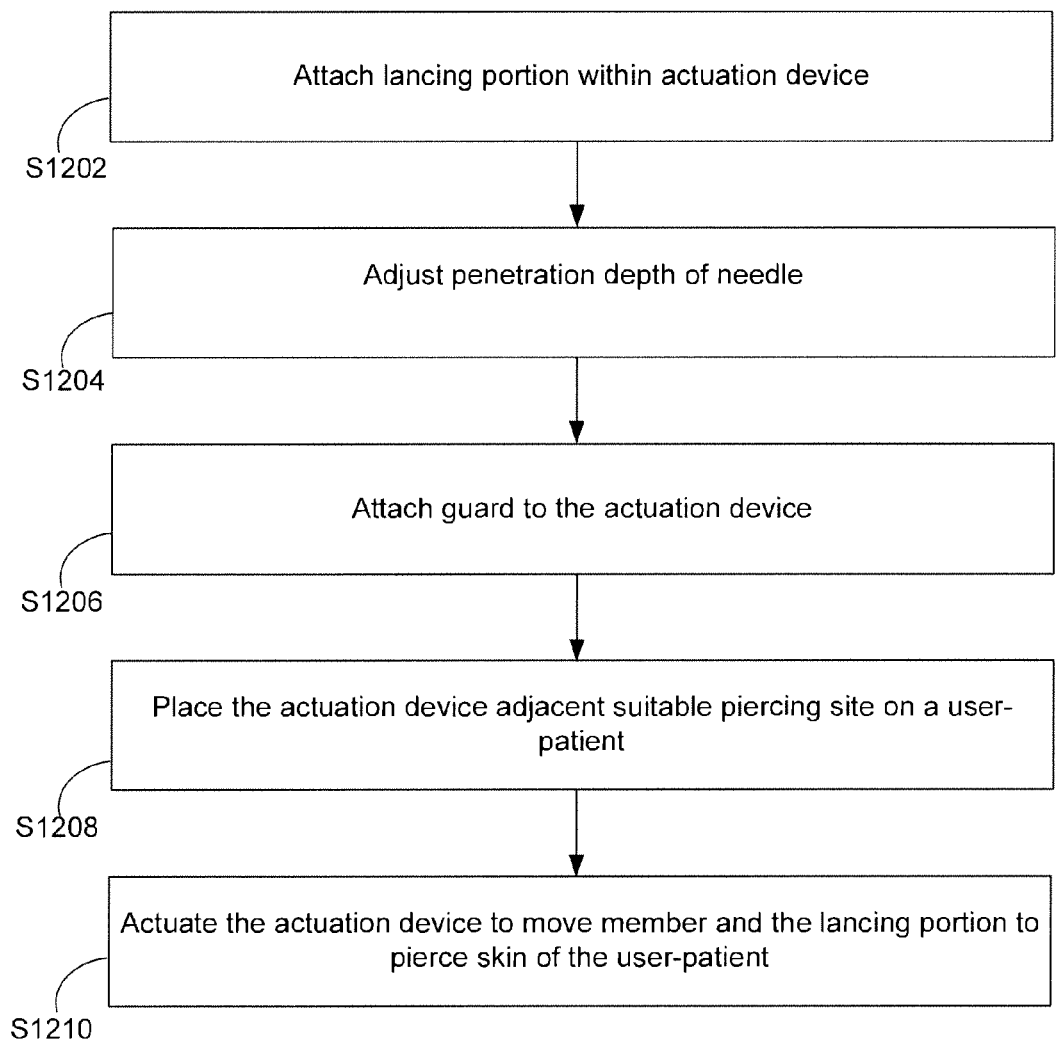
FIG. 24 illustrates flow chart for using a medial device in accordance with an embodiment of the present invention.

FIG. 24 illustrates a flowchart for using an actuation device according to an embodiment of the present invention. With reference to FIGS. 22-24, in step S1202, the lancing portion 350 may be attached to the actuation device 390. In step S1204, the penetration depth of the needle 354 may be adjusted.

Next in step S1206, the guard 330 may be attached to the actuation device 390. In step S1208, the actuation device 390 may be placed adjacent a suitable injection site on the user-patient. In step S1210, the member 398 and the lancing portion 350 may be actuated to prick the user-patient at the injection site. In further embodiments, the lancing portion 350 may be removed from the actuation device 390, and the actuation device 390 may used similar to the actuation device 290 and an infusion set, such as, but not limited to, the system 200 described with respect to FIGS. 17-21.

Figure 25:
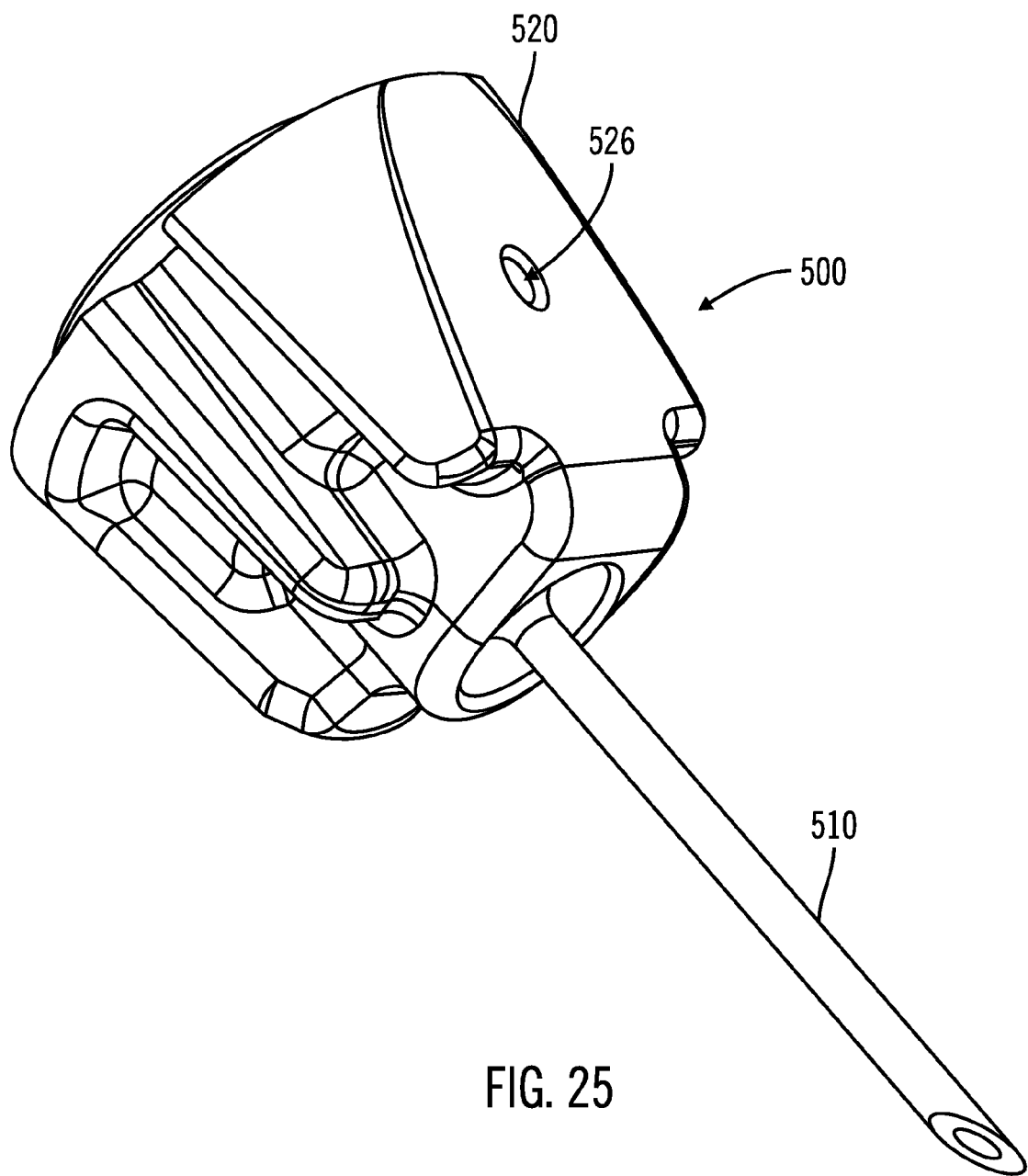
FIG. 25 illustrates a medial device in accordance with an embodiment of the present invention.
Figure 26:
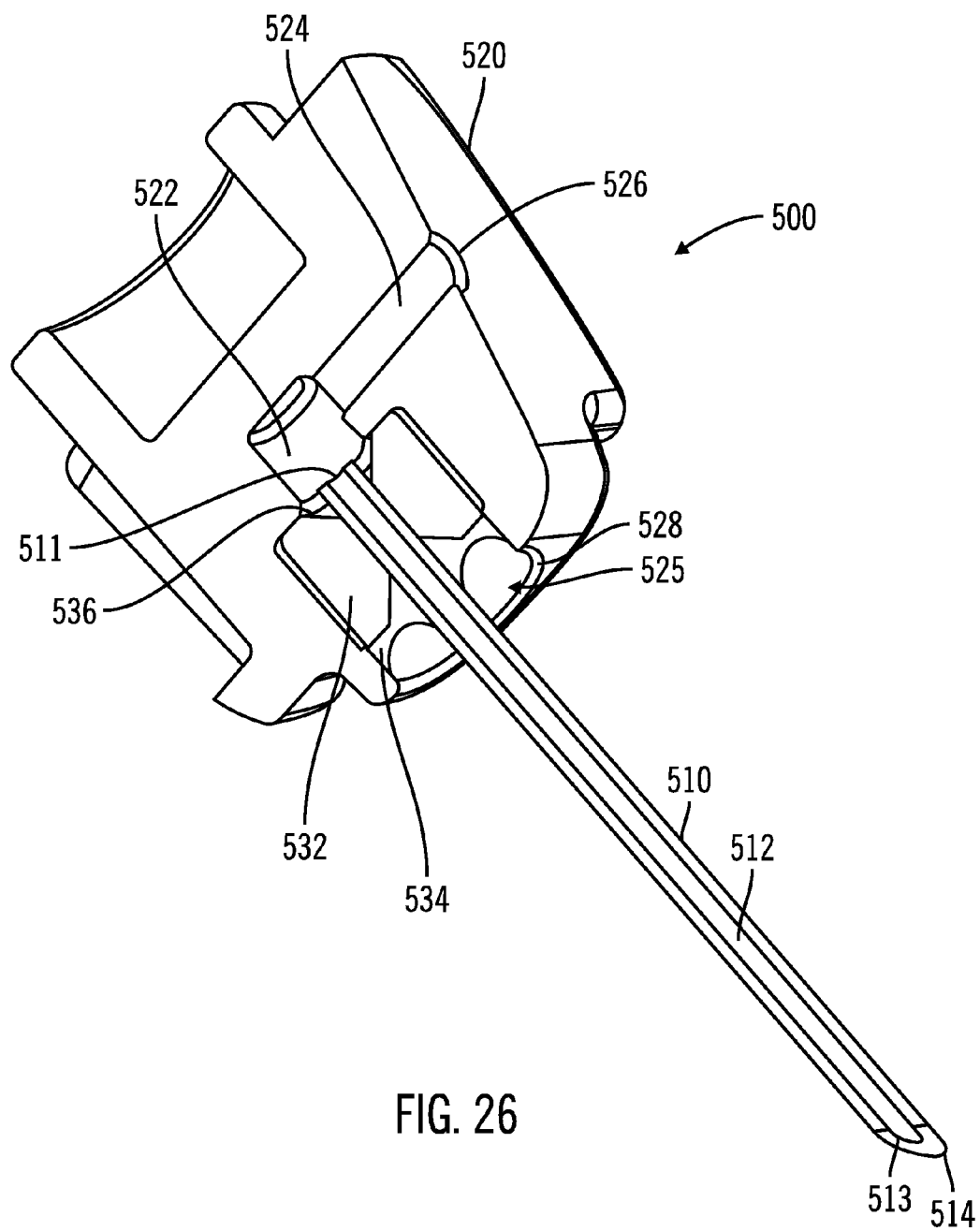
FIG. 26 illustrates a medial device in accordance with an embodiment of the present invention.

FIGS. 25 and 26 illustrate a needle assembly 500 according to an embodiment of the present invention. Although the needle assembly 500 may be similar or used with the embodiments of FIGS. 17-24, it should be understood that the needle assembly 500 may also include some or all of the same components and operate in a manner similar to that shown and described in the embodiments of FIGS. 1-16. In addition, some or all of the features shown in FIGS. 1-24 may be combined in various ways and included in the embodiment shown in FIGS. 25 and 26. The needle assembly 500 may include, but is not limited to, a needle (or cannula) 510 and a housing 520.

The needle 510 may be arranged within the housing 520. For example, the needle 510 may extend through at least a portion of the housing 520. The needle 510 may have a hollow central channel 512 extending along a longitudinal length of the needle 510. The needle 510 may have a first opening 511 and a second opening 513 for communicating with the hollow central channel 512. In some embodiments, the second opening 513 may be located at, but not limited to, a sharp end 514 of the needle 510. The first opening 511 may be located at, but is not limited to, an end of the hollow central channel 512 opposite the sharp end 514. The needle 510 may be made of any suitably rigid material, including, but not limited to metal, plastic, ceramic, or the like.

The housing 520 may be made of any suitably rigid material, including, but not limited to plastic, metal, ceramic, composite material, or the like. In some embodiments, the housing 520 may include a cavity 525, a chamber 522, a channel 524, and an opening 526. The opening 526 may be arranged on an exterior surface of the housing 520 for alignment with a fluid flow path, such as, but not limited to, the fluid conduit 224 (e.g., FIGS. 17-21) to convey fluidic media, for example, from a reservoir (not shown) containing fluidic media. The opening 526 may open into the channel 524.

The channel 524 may be in alignment with the chamber 522. The chamber 522 may be in communication or alignment with the hollow central channel 512 of the needle 510. Accordingly, a flow path may be established between the opening 526 and the hollow central channel 512 of the needle 510 via the channel 524 and the chamber 522.

The cavity 525 may be arranged within the housing 520 such that at least a portion of the needle 510 extends through the cavity 525. The cavity 525 may contain a compliant material 532 adjacent a portion of the needle 510. The needle 510 may be arranged to be substantially free floating within or along the compliant material 532. In other words in some embodiments, the needle 510 generally may be free from contacting the housing 520; rather, the needle 510 may be by the compliant material 532.

The compliant material 532, which may be any suitable flexible material, such as but not limited to, silicone, other flexible polymers, or the like, may be sufficiently flexible, pliable, compressible, resilient, or the like to allow articulation (e.g., pivotal movement) of the needle 510 through and/or against the compliant material 532 relative to the housing 520 in one or more directions. Allowing articulation of the needle 510 may help prevent the needle 510 from "kinking" or otherwise bending, for example, in a case where the needle 510 is attached to a user-patient and the needle 510 and/or the housing 520 are/is moved (e.g., laterally) relative to each other. For instance, in some embodiments, the compliant material 532 may be sufficiently viscous to support or otherwise be in contact with the needle 510, but allow some articulation or movement (e.g., angular and/or lateral) of the needle 510.

In further embodiments, the compliant material 532 may be any sufficiently strong or rigid material to support the needle 510 as the needle 510 pierces and/or remains in the skin of the user-patient. In such embodiments, the compliant material 532 may keep the needle 510 sufficiently steady relative to the housing 520 while still allowing articulation of the needle 510 relative to the housing 520.

In further embodiments, the compliant material 532 may provide an adhering function to adhere to the needle 510 and/or the housing 520. Accordingly, the needle 510 may be supported by the compliant material 532 so that the needle 510 can be sufficiently free floating within the chamber 525 of the housing 520 to be moveable relative to the housing 520. In other embodiments, the compliant material 532 may be adhered to the needle 510 and/or the housing 520.

In some embodiments, the compliant material 532 may be adapted to provide a sealing function to prevent fluidic media from flowing between the compliant material 532 and the needle 510 and/or the housing 520. Accordingly, in a case where the needle 510 is in a user-patient and the needle 510 and/or the housing 520 are moved (e.g., laterally) relative to each other, the needle 510 can articulate (e.g., pivot) relative to the housing 520 while inhibiting fluidic media from flowing between the compliant material 532 and the needle 510 and/or the housing 520. In further embodiments, the compliant material 532 may be a seal member located within the cavity 525 (or outside the cavity 525) to inhibit fluidic media from flowing between the compliant material 532 and the needle 510 and/or the housing 520.

In some embodiments, a seal member, such as an o-ring or the like may be arranged between the needle 510 and the compliant material 532 to inhibit fluidic media from flowing between the seal member and the needle 510. In some embodiments, the seal member may be arranged between the compliant material 532 and the housing 520 to inhibit fluidic media from flowing between the seal member and the housing 520.

In various embodiments, the chamber 524 may have a width dimension greater than a width dimension of the hollow central channel 512 of the needle 510. Because the width dimension of the chamber 522 may be greater than the width dimension of the hollow central channel 512 of the needle 510, the chamber 522 and the hollow central channel 512 may remain in alignment when the needle 510 is articulated. Thus, whether the needle 510 is centered relative to the chamber 524 (e.g., substantially perpendicular to the chamber 522), angled (e.g., at an acute angle to the chamber 522), or off-center (e.g., offset from a center point of the chamber 525), fluidic media may be able to flow from the chamber 522 to the needle 510.

In some embodiments, the compliant material 532 have a recess 536 formed therein. The recess 526 may be in communication with the chamber 524 and the first end 511 of the needle 510. In further embodiments, the recess 536 may be defined by a sloped surface. In yet further embodiments, the surface (or a portion thereof) of the recess 536 may be sloped to correspond generally to a maximum angle of movement of the needle 510 relative to the housing 520. For example, in a case where the needle assembly 500 is configured to allow the needle 510 to articulate relative to the housing 520 up to, for example, thirty degrees (relative the orientation shown, for example in FIG. 26), the surface (or a portion thereof) may likewise be sloped to match this angle. Thus, even in a case where the needle 510 is articulated relative to the housing 520, for example thirty degrees, fluidic media may be able to flow from the chamber 522 to the needle 510.

In some embodiments, the compliant material 532 may be retained within the cavity 525 with a retaining member 534, such as a septum, cap, glue joint, or the like. In further embodiments, the retaining member 534 may be adapted to be sufficiently flexible, pliable, compressible, resilient, or the like to allow articulation of the needle 510 and/or to provide a sealing ability similar to that described with respect to the first material 532.

In some embodiments, in a case where the needle 510 is in a user-patient and the needle 510 and/or the housing 520 are/is moved (e.g., laterally) relative to each other, the needle 510 and/or the housing 510 may be adapted so that the housing 520 remains substantially motionless. Accordingly in such embodiments, the needle 510 may articulate (e.g., pivot) relative to the housing. In some embodiments, in a case where the needle 510 is in a user-patient and the needle 510 and/or the housing 520 are moved (e.g., laterally) relative to each other, the needle 510 and/or the housing 510 may be adapted so that the needle 510 remains substantially motionless. Accordingly in such embodiments, the housing 520 may articulate (e.g., pivot) relative to the needle 510.

In some embodiments, the housing 510 in its entirety or a portion thereof may be made of a material adapted to allow articulation of the needle 510 and/or the housing 520 relative to each other and/or provide a sealing ability like the compliant material 532. The material may be made of a similar or a different material from the compliant material 532. In such embodiments, the chamber 522, the channel 524, and/or the opening 526 may be formed on or within the compliant material 524. In further embodiments, a retaining member, such as the retaining member 534, or the like may be provided to provide structure to the compliant material 532 and/or to otherwise retain the seal member housing 510 to a confined space, for example.

In various embodiments, the needle assembly 500 may be similar to the insert structure 260 previously described with respect to FIGS. 17-21. With reference to FIGS. 17-26, in some embodiments, the needle assembly 500 may replace the insert structure 260. In such embodiments, the needle 510 may serve as the needle 246 and the cannula 246. As such, once the needle assembly 500 (or insert structure 260) is moved to the second position, the needle 510 may remain in the user-patient without having to be retracted like the needle 246. In the second position, for example, the channel 524 may align with the fluid conduit 224 that may establish a fluid flow path with a reservoir for conveying fluidic media to the user-patient or receiving fluidic media from the user-patient. In further embodiments, the needle assembly 500 may be configured to include an engagement portion, such as the handle 289 of the plunger head 288, or the like, for engaging the actuation device 290 (or 390) so that the actuation device 290 (or 390) can cause movement of the needle assembly 500 to the second position.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. An insertion system, the insertion system comprising:
   a housing;
   a piercing member arranged partially within the housing, the piercing member having a piercing end located outside of the housing for piercing a membrane, the piercing member having a hollow interior for conveying fluidic media; and
   a compliant material arranged within the housing to support the piercing member and attach the piercing member to the housing, the compliant material for allowing articulation of the piercing member relative to the housing in a case where the piercing member is in the membrane and moved relative to the housing;
   wherein the piercing member extends through the compliant material and has a first end located on an opposite side of the compliant material with respect to the piercing end of the piercing member.

2. The insertion system of claim 1, the compliant material provides a fluid seal between the piercing member and the compliant material and between the housing and the compliant material, to substantially prevent fluidic media from flowing between the compliant material and the piercing member, and between the compliant material and the housing.

3. The insertion system of claim 1, the compliant material forms a fluid seal with the housing and with the piercing member.

4. The insertion system of claim 1, the compliant material arranged to support the piercing member such that the piercing member does not contact the housing.

5. The insertion system of claim 1, wherein the piercing member comprises a needle.

6. The insertion system of claim 1, the housing having a fluid channel for alignment with a reservoir, the fluid channel in fluid communication with a hollow interior of the piercing member.

7. The insertion system of claim 1, the housing having a chamber for receiving fluidic media, the chamber located on one side of the compliant material; and the compliant material having a surface defining an inner wall of the chamber for contacting fluidic media received within the chamber.

8. The insertion system of claim 1, the insertion system further comprising:
   a retaining member for retaining the compliant material within the housing.

9. The insertion system of claim 8, wherein the retaining member comprises at least one of a cap, glue joint, and a septum.

10. The insertion system of claim 1, wherein the housing is made of the compliant material to allow articulation of the piercing member relative to the housing in a case where the piercing member is moved relative to the housing.

11. The insertion system of claim 1, wherein the membrane comprises skin of a patient, the compliant material for allowing articulation of the piercing member relative to the housing in a case where the piercing member is in the skin of the patient and moved relative to the housing.

12. The insertion system of claim 1, wherein a fluid flow passage is provided through at least a portion of the compliant material.

13. The insertion system of claim 1, the complaint material being adhered to the housing, to remain in a fixed position relative to the housing.

14. The insertion system of claim 1, the piercing member having a longitudinal dimension that extends out from the housing such that a portion of the piercing member is located within the housing and another portion of the piercing member is located external to the housing.

15. The insertion system of claim 1, the piercing member having a hollow central channel and first and second openings in communication with the central channel of the piercing member; and
   the housing having an internal channel and an external opening in fluid flow communication with the internal channel, for connection with an external fluid flow path, the internal channel being in fluid flow communication with the first opening of the piercing member.

16. The insertion system of claim 1, further comprising a needle to place the piercing member in the membrane.

17. The insertion system of claim 1, wherein the piercing member and the complaint material is in the housing as the fluidic media passes through the hollow interior of the piercing member.

18. The insertion system of claim 1, wherein:
   the piercing member has a longitudinal dimension extending along a length dimension of the housing, at an angle of orientation relative to the length dimension of the housing; and
   the compliant material allows articulation of the piercing member in a direction that changes the angle of orientation of the longitudinal dimension of the piercing member relative to the length dimension of the housing.

19. The insertion system of claim 18, wherein the compliant material allows articulation of the piercing member by an amount that changes the angle of orientation of the longitudinal dimension of the piercing member relative to the length dimension of the housing by up to 30 degrees.

20. The insertion system of claim 1, wherein:
   the piercing member has a longitudinal dimension extending along a length dimension of the housing; and
   the compliant material allows articulation of the piercing member in a direction lateral to the length dimension of the housing.

21. The insertion system of claim 1, wherein the housing has a chamber for receiving a fluidic media, the compliant material has a surface defining an inner wall of the chamber, the inner wall arranged for contacting fluidic media received in the chamber.

22. The insertion system of claim 21, wherein the surface of the compliant material that defines the inner wall of the chamber has a recess arranged for contacting fluidic media received in the chamber, and wherein the first end of the piercing member extends into the recess.

23. An insertion system comprising:
   a housing;
   a piercing member arranged at least partially within the housing, the piercing member having a piercing end located outside of the housing for piercing a membrane, the piercing member having a first end opposite the piercing end; and
   a compliant material arranged within the housing to support the piercing member, the compliant material for allowing articulation of the piercing member relative to the housing in a case where the piercing member is in the membrane and moved relative to the housing;
   wherein piercing member extends through the compliant material
   wherein the housing includes a chamber for receiving fluidic media, the chamber located on one side of the compliant material; and
   wherein the first end of the piercing member is located in the chamber and outside of the compliant material, the first end has an opening to the hollow interior of the piercing member, and the opening remains outside of the compliant material and in fluid flow communication with the chamber.

24. The insertion system of claim 23, wherein the compliant material forms at least one inner wall of the chamber for contacting fluidic media received in the chamber.

25. The insertion system of claim 23, wherein the compliant material has a surface defining an inner wall of the chamber, the surface having a recess for contacting fluidic media received in the chamber, the first end of the piercing member extending in the recess.

26. The insertion system of claim 23, the compliant material forms a fluid seal with the housing and with the piercing member.

27. An insertion system comprising:
   a housing;
   a piercing member arranged at least partially within the housing, the piercing member for piercing a membrane; and
   a compliant material arranged within the housing to support the piercing member, the compliant material for allowing articulation of the piercing member relative to the housing in a case where the piercing member is in the membrane and moved relative to the housing;
   the piercing member having a first opening and a second opening, one of the first opening and the second opening for receiving fluidic media into a hollow interior of the piercing member, the other of the one of the first opening and the second opening for allowing the fluidic media to exit the hollow interior of the piercing member;
   the compliant material having a body for supporting the piercing member; the body having a recess in fluid flow communication with one of the first opening and the second opening, the recess defined by a surface sloped to correspond generally to an angle of articulation of the piercing member relative to the housing;
   wherein the housing is attachable to a base that secures to the membrane with an adhesive material when the piercing member pierces the membrane, and wherein the membrane is skin of a patient.

28. The insertion system of claim 27, the piercing member having a piercing end located outside of the housing.

29. A method of making an insertion system, the method comprising:
   providing a housing;
   arranging a piercing member at least partially within the housing, the piercing member having a first end and a piercing end, the piercing end being located outside of the housing for piercing a membrane, the piercing member having a hollow interior for conveying fluidic media; and
   arranging a compliant material within the housing and attaching the piercing member to the housing with the compliant material, to support the piercing member with the compliant material in the housing, the compliant material for allowing articulation of the piercing member relative to the housing in a case where the piercing member is in the membrane and moved relative to the housing;
   wherein arranging the piercing member comprises extending the piercing member through the compliant material, such that the first end of the piercing member is located outside of the compliant material, on an opposite side of the compliant material with respect to the piercing end of the piercing member.

* * * * *